United States Patent
Roffler et al.

(10) Patent No.: US 10,604,747 B2
(45) Date of Patent: Mar. 31, 2020

(54) ENGINEERED ENZYME FOR ENZYME REPLACEMENT THERAPY

(71) Applicant: Academia Sinica, Taipei (TW)

(72) Inventors: Steve Roffler, Taipei (TW); Huai-Yao Chuang, Taoyuan (TW)

(73) Assignee: Academia Sinica, Taipei (TW)

( * ) Notice: Subject to any disclaimer, the term of this patent is extended or adjusted under 35 U.S.C. 154(b) by 37 days.

(21) Appl. No.: 15/750,753

(22) PCT Filed: Aug. 5, 2016

(86) PCT No.: PCT/US2016/045715
§ 371 (c)(1),
(2) Date: Feb. 6, 2018

(87) PCT Pub. No.: WO2017/024204
PCT Pub. Date: Feb. 9, 2017

(65) Prior Publication Data
US 2018/0346896 A1    Dec. 6, 2018

Related U.S. Application Data

(60) Provisional application No. 62/201,889, filed on Aug. 6, 2015.

(51) Int. Cl.
*C12N 9/24* (2006.01)
*C12Q 1/40* (2006.01)
*A61K 38/00* (2006.01)

(52) U.S. Cl.
CPC .............. *C12N 9/2402* (2013.01); *C12N 9/24* (2013.01); *C12Q 1/40* (2013.01); *C12Y 302/01031* (2013.01); *C12Y 302/01076* (2013.01); *A61K 38/00* (2013.01)

(58) Field of Classification Search
None
See application file for complete search history.

(56) References Cited

U.S. PATENT DOCUMENTS

| | | |
|---|---|---|
| 9,920,306 B2 * | 3/2018 | Lee ................ C12N 9/2402 |
| 2004/0191867 A1 | 9/2004 | Lindahl et al. |
| 2009/0041741 A1 | 2/2009 | Sly et al. |
| 2010/0221235 A1 | 9/2010 | Arranz |
| 2014/0377246 A1 | 12/2014 | Tomatsu et al. |

OTHER PUBLICATIONS

Naz, et al., "Human beta-glucuronidase: structure, function, and application in enzyme replacement therapy", Rejuvenation Research, 2013, vol. 16, No. 5, pp. 352-363.

* cited by examiner

*Primary Examiner* — Anand U Desai
(74) *Attorney, Agent, or Firm* — Cesari and McKenna, LLP

(57) ABSTRACT

An engineered enzyme, comprising an amino acid sequence that is at least 80% identical to the amino acid sequence of a human beta-glucuronidase, wherein the engineered enzyme exhibits a higher level of alpha-iduronidase enzymatic activity as compared to the human beta-glucuronidase.

8 Claims, 10 Drawing Sheets
Specification includes a Sequence Listing.

A

B

C

D

E

SEQUENCE LISTING

```
<160> NUMBER OF SEQ ID NOS: 4

<210> SEQ ID NO 1
<211> LENGTH: 1956
<212> TYPE: DNA
<213> ORGANISM: Homo sapiens
<220> FEATURE:
<221> NAME/KEY: CDS
<222> LOCATION: (1)..(1956)
<220> FEATURE:
<221> NAME/KEY: misc_feature
<222> LOCATION: (1)..(1956)
<223> OTHER INFORMATION: beta-glucuronidase

<400> SEQUENCE: 1 atg gcc cgg ggg tcg gcg gtt gcc tgg gcg gcg ctc ggg ccg ttg ttg      48
Met Ala Arg Gly Ser Ala Val Ala Trp Ala Ala Leu Gly Pro Leu Leu
1               5                   10                  15 tgg ggc tgc gcg ctg ggg ctg cag ggc ggg atg ctg tac ccc cag gag      96
Trp Gly Cys Ala Leu Gly Leu Gln Gly Gly Met Leu Tyr Pro Gln Glu
                20                  25                  30 agc ccg tcg cgg gag tgc aag gag ctg gac ggc ctc tgg agc ttc cgc     144
Ser Pro Ser Arg Glu Cys Lys Glu Leu Asp Gly Leu Trp Ser Phe Arg
            35                  40                  45 gcc gac ttc tct gac aac cga cgc cgg ggc ttc gag gag cag tgg tac     192
Ala Asp Phe Ser Asp Asn Arg Arg Gly Phe Glu Glu Gln Trp Tyr
        50                  55                  60 cgg cgg ccg ctg tgg gag tca ggc ccc acc gtg gac atg cca gtt ccc     240
Arg Arg Pro Leu Trp Glu Ser Gly Pro Thr Val Asp Met Pro Val Pro
65                  70                  75                  80 tcc agc ttc aat gac atc agc cag gac tgg cgt ctg cgg cat ttt gtc     288
Ser Ser Phe Asn Asp Ile Ser Gln Asp Trp Arg Leu Arg His Phe Val
                85                  90                  95 ggc tgg gtg tgg tac gaa cgg gag gtg atc ctg ccg gag cga tgg acc     336
Gly Trp Val Trp Tyr Glu Arg Glu Val Ile Leu Pro Glu Arg Trp Thr
```

```
                100                 105                 110
cag gac ctg cgc aca aga gtg gtg ctg agg att ggc agt gcc cat tcc       384
Gln Asp Leu Arg Thr Arg Val Val Leu Arg Ile Gly Ser Ala His Ser
        115                 120                 125 tat gcc atc gtg tgg gtg aat ggg gtc gac acg cta gag cat gag ggg       432
Tyr Ala Ile Val Trp Val Asn Gly Val Asp Thr Leu Glu His Glu Gly
130                 135                 140 ggc tac ctc ccc ttc gag gcc gac atc agc aac ctg gtc cag gtg ggg       480
Gly Tyr Leu Pro Phe Glu Ala Asp Ile Ser Asn Leu Val Gln Val Gly
145                 150                 155                 160 ccc ctg ccc tcc cgg ctc cga atc act atc gcc atc aac aac aca ctc       528
Pro Leu Pro Ser Arg Leu Arg Ile Thr Ile Ala Ile Asn Asn Thr Leu
                165                 170                 175 acc ccc acc acc ctg cca cca ggg acc atc caa tac ctg act gac acc       576
Thr Pro Thr Thr Leu Pro Pro Gly Thr Ile Gln Tyr Leu Thr Asp Thr
            180                 185                 190 tcc aag tat ccc aag ggt tac ttt gtc cag aac aca tat ttt gac ttt       624
Ser Lys Tyr Pro Lys Gly Tyr Phe Val Gln Asn Thr Tyr Phe Asp Phe
        195                 200                 205 ttc aac tac gct gga ctg cag cgg tct gta ctt ctg tac acg aca ccc       672
Phe Asn Tyr Ala Gly Leu Gln Arg Ser Val Leu Leu Tyr Thr Thr Pro
210                 215                 220 acc acc tac atc gat gac atc acc gtc acc acc agc gtg gag caa gac       720
Thr Thr Tyr Ile Asp Asp Ile Thr Val Thr Thr Ser Val Glu Gln Asp
225                 230                 235                 240 agt ggg ctg gtg aat tac cag atc tct gtc aag ggc agt aac ctg ttc       768
Ser Gly Leu Val Asn Tyr Gln Ile Ser Val Lys Gly Ser Asn Leu Phe
                245                 250                 255 aag ttg gaa gtg cgt ctt ttg gat gca gaa aac aaa gtc gtg gcg aat       816
Lys Leu Glu Val Arg Leu Leu Asp Ala Glu Asn Lys Val Val Ala Asn
            260                 265                 270 ggg act ggg acc cag ggc caa ctt aag gtg cca ggt gtc agc ctc tgg       864
Gly Thr Gly Thr Gln Gly Gln Leu Lys Val Pro Gly Val Ser Leu Trp
        275                 280                 285 tgg ccg tac ctg atg cac gaa cgc cct gcc tat ctg tat tca ttg gag       912
Trp Pro Tyr Leu Met His Glu Arg Pro Ala Tyr Leu Tyr Ser Leu Glu
290                 295                 300 gtg cag ctg act gca cag acg tca ctg ggg cct gtg tct gac ttc tac       960
Val Gln Leu Thr Ala Gln Thr Ser Leu Gly Pro Val Ser Asp Phe Tyr
305                 310                 315                 320 aca ctc cct gtg ggg atc cgc act gtg gct gtc acc aag agc cag ttc      1008
Thr Leu Pro Val Gly Ile Arg Thr Val Ala Val Thr Lys Ser Gln Phe
                325                 330                 335 ctc atc aat ggg aaa cct ttc tat ttc cac ggt gtc aac aag cat gag      1056
Leu Ile Asn Gly Lys Pro Phe Tyr Phe His Gly Val Asn Lys His Glu
            340                 345                 350 gat gcg gac atc cga ggg aag ggc ttc gac tgg ccg ctg ctg gtg aag      1104
Asp Ala Asp Ile Arg Gly Lys Gly Phe Asp Trp Pro Leu Leu Val Lys
        355                 360                 365 gac ttc aac ctg ctt cgc tgg ctt ggt gcc aac gct ttc cgt acc agc      1152
Asp Phe Asn Leu Leu Arg Trp Leu Gly Ala Asn Ala Phe Arg Thr Ser
370                 375                 380 cac tac ccc tat gca gag gaa gtg atg cag atg tgt gac cgc tat ggg      1200
His Tyr Pro Tyr Ala Glu Glu Val Met Gln Met Cys Asp Arg Tyr Gly
385                 390                 395                 400 att gtg gtc atc gat gag tgt ccc ggc gtg ggc ctg gcg ctg ccg cag      1248
Ile Val Val Ile Asp Glu Cys Pro Gly Val Gly Leu Ala Leu Pro Gln
                405                 410                 415 ttc ttc aac aac gtt tct ctg cat cac cac atg cag gtg atg gaa gaa      1296
```

```
                Phe Phe Asn Asn Val Ser Leu His His His Met Gln Val Met Glu Glu
                                420                 425                 430 gtg gtg cgt agg gac aag aac cac ccc gcg gtc gtg atg tgg tct gtg                 1344
Val Val Arg Arg Asp Lys Asn His Pro Ala Val Val Met Trp Ser Val
            435                 440                 445 gcc aac gag cct gcg tcc cac cta gaa tct gct ggc tac tac ttg aag                 1392
Ala Asn Glu Pro Ala Ser His Leu Glu Ser Ala Gly Tyr Tyr Leu Lys
450                 455                 460 atg gtg atc gct cac acc aaa tcc ttg gac ccc tcc cgg cct gtg acc                 1440
Met Val Ile Ala His Thr Lys Ser Leu Asp Pro Ser Arg Pro Val Thr
465                 470                 475                 480 ttt gtg agc aac tct aac tat gca gca gac aag ggg gct ccg tat gtg                 1488
Phe Val Ser Asn Ser Asn Tyr Ala Ala Asp Lys Gly Ala Pro Tyr Val
            485                 490                 495 gat gtg atc tgt ttg aac agc tac tac tct tgg tat cac gac tac ggg                 1536
Asp Val Ile Cys Leu Asn Ser Tyr Tyr Ser Trp Tyr His Asp Tyr Gly
500                 505                 510 cac ctg gag ttg att cag ctg cag ctg gcc acc cag ttt gag aac tgg                 1584
His Leu Glu Leu Ile Gln Leu Gln Leu Ala Thr Gln Phe Glu Asn Trp
            515                 520                 525 tat aag aag tat cag aag ccc att att cag agc gag tat gga gca gaa                 1632
Tyr Lys Lys Tyr Gln Lys Pro Ile Ile Gln Ser Glu Tyr Gly Ala Glu
530                 535                 540 acg att gca ggg ttt cac cag gat cca cct ctg atg ttc act gaa gag                 1680
Thr Ile Ala Gly Phe His Gln Asp Pro Pro Leu Met Phe Thr Glu Glu
545                 550                 555                 560 tac cag aaa agt ctg cta gag cag tac cat ctg ggt ctg gat caa aaa                 1728
Tyr Gln Lys Ser Leu Leu Glu Gln Tyr His Leu Gly Leu Asp Gln Lys
            565                 570                 575 cgc aga aaa tac gtg gtt gga gag ctc att tgg aat ttt gcc gat ttc                 1776
Arg Arg Lys Tyr Val Val Gly Glu Leu Ile Trp Asn Phe Ala Asp Phe
            580                 585                 590 atg act gaa cag tca ccg acg aga gtg ctg ggg aat aaa aag ggg atc                 1824
Met Thr Glu Gln Ser Pro Thr Arg Val Leu Gly Asn Lys Lys Gly Ile
            595                 600                 605 ttc act cgg cag aga caa cca aaa agt gca gcg ttc ctt ttg cga gag                 1872
Phe Thr Arg Gln Arg Gln Pro Lys Ser Ala Ala Phe Leu Leu Arg Glu
610                 615                 620 aga tac tgg aag att gcc aat gaa acc agg tat ccc cac tca gta gcc                 1920
Arg Tyr Trp Lys Ile Ala Asn Glu Thr Arg Tyr Pro His Ser Val Ala
625                 630                 635                 640 aag tca caa tgt ttg gaa aac agc ctg ttt act tga                                 1956
Lys Ser Gln Cys Leu Glu Asn Ser Leu Phe Thr
            645                 650

<210> SEQ ID NO 2
<211> LENGTH: 651
<212> TYPE: PRT
<213> ORGANISM: Homo sapiens

<400> SEQUENCE: 2

Met Ala Arg Gly Ser Ala Val Ala Trp Ala Leu Gly Pro Leu Leu
1               5                   10                  15

Trp Gly Cys Ala Leu Gly Leu Gln Gly Gly Met Leu Tyr Pro Gln Glu
                20                  25                  30

Ser Pro Ser Arg Glu Cys Lys Glu Leu Asp Gly Leu Trp Ser Phe Arg
            35                  40                  45

Ala Asp Phe Ser Asp Asn Arg Arg Arg Gly Phe Glu Glu Gln Trp Tyr
        50                  55                  60
```

```
Arg Arg Pro Leu Trp Glu Ser Gly Pro Thr Val Asp Met Pro Val Pro
 65                  70                  75                  80

Ser Ser Phe Asn Asp Ile Ser Gln Asp Trp Arg Leu Arg His Phe Val
                 85                  90                  95

Gly Trp Val Trp Tyr Glu Arg Glu Val Ile Leu Pro Glu Arg Trp Thr
            100                 105                 110

Gln Asp Leu Arg Thr Arg Val Val Leu Arg Ile Gly Ser Ala His Ser
        115                 120                 125

Tyr Ala Ile Val Trp Val Asn Gly Val Asp Thr Leu Glu His Glu Gly
    130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
                180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
                260                 265                 270

Gly Thr Gly Thr Gln Gly Gln Leu Lys Val Pro Gly Val Ser Leu Trp
            275                 280                 285

Trp Pro Tyr Leu Met His Glu Arg Pro Ala Tyr Leu Tyr Ser Leu Glu
        290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
                340                 345                 350

Asp Ala Asp Ile Arg Gly Lys Gly Phe Asp Trp Pro Leu Leu Val Lys
            355                 360                 365

Asp Phe Asn Leu Leu Arg Trp Leu Gly Ala Asn Ala Phe Arg Thr Ser
    370                 375                 380

His Tyr Pro Tyr Ala Glu Glu Val Met Gln Met Cys Asp Arg Tyr Gly
385                 390                 395                 400

Ile Val Val Ile Asp Glu Cys Pro Gly Val Gly Leu Ala Leu Pro Gln
                405                 410                 415

Phe Phe Asn Asn Val Ser Leu His His Met Gln Val Met Glu Glu
                420                 425                 430

Val Val Arg Arg Asp Lys Asn His Pro Ala Val Val Met Trp Ser Val
            435                 440                 445

Ala Asn Glu Pro Ala Ser Leu His Leu Glu Ser Ala Gly Tyr Tyr Leu Lys
                450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
```

```
                        485                 490                 495
Asp Val Ile Cys Leu Asn Ser Tyr Tyr Ser Trp Tyr His Asp Tyr Gly
                500                 505                 510

His Leu Glu Leu Ile Gln Leu Gln Leu Ala Thr Gln Phe Glu Asn Trp
            515                 520                 525

Tyr Lys Lys Tyr Gln Lys Pro Ile Ile Gln Ser Glu Tyr Gly Ala Glu
        530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
                580                 585                 590

Met Thr Glu Gln Ser Pro Thr Arg Val Leu Gly Asn Lys Lys Gly Ile
            595                 600                 605

Phe Thr Arg Gln Arg Gln Pro Lys Ser Ala Ala Phe Leu Leu Arg Glu
        610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Leu Phe Thr
                645                 650

<210> SEQ ID NO 3
<211> LENGTH: 1962
<212> TYPE: DNA
<213> ORGANISM: Homo sapiens
<220> FEATURE:
<221> NAME/KEY: CDS
<222> LOCATION: (1)..(1962)
<220> FEATURE:
<221> NAME/KEY: misc_feature
<222> LOCATION: (1)..(1962)
<223> OTHER INFORMATION: alpha-iduronidase

<400> SEQUENCE: 3 atg cgt ccc ctg cgc ccc cgc gcc gcg ctg ctg gcg ctc ctg gcc tcg      48
Met Arg Pro Leu Arg Pro Arg Ala Ala Leu Leu Ala Leu Leu Ala Ser
1               5                   10                  15 ctc ctg gcc gcg ccc ccg gtg gcc ccg gcc gag gcc ccg cac ctg gtg      96
Leu Leu Ala Ala Pro Pro Val Ala Pro Ala Glu Ala Pro His Leu Val
                20                  25                  30 cat gtg gac gcg gcc cgc gcg ctg tgg ccc ctg cgg cgc ttc tgg agg     144
His Val Asp Ala Ala Arg Ala Leu Trp Pro Leu Arg Arg Phe Trp Arg
            35                  40                  45 agc aca ggc ttc tgc ccc ccg ctg cca cac agc cag gct gac cag tac     192
Ser Thr Gly Phe Cys Pro Pro Leu Pro His Ser Gln Ala Asp Gln Tyr
        50                  55                  60 gtc ctc agc tgg gac cag cag ctc aac ctc gcc tat gtg ggc gcc gtc     240
Val Leu Ser Trp Asp Gln Gln Leu Asn Leu Ala Tyr Val Gly Ala Val
65                  70                  75                  80 cct cac cgc ggc atc aag cag gtc cgg acc cac tgg ctg ctg gag ctt     288
Pro His Arg Gly Ile Lys Gln Val Arg Thr His Trp Leu Leu Glu Leu
                85                  90                  95 gtc acc acc agg ggg tcc act gga cgg ggc ctg agc tac aac ttc acc     336
Val Thr Thr Arg Gly Ser Thr Gly Arg Gly Leu Ser Tyr Asn Phe Thr
                100                 105                 110 cac ctg gac ggg tac ctg gac ctt ctc agg gag aac cag ctc ctc cca     384
His Leu Asp Gly Tyr Leu Asp Leu Leu Arg Glu Asn Gln Leu Leu Pro
            115                 120                 125
```

```
ggg ttt gag ctg atg ggc agc gcc tcg ggc cac ttc act gac ttt gag      432
Gly Phe Glu Leu Met Gly Ser Ala Ser Gly His Phe Thr Asp Phe Glu
    130                 135                 140 gac aag cag cag gtg ttt gag tgg aag gac ttg gtc tcc agc ctg gcc      480
Asp Lys Gln Gln Val Phe Glu Trp Lys Asp Leu Val Ser Ser Leu Ala
145                 150                 155                 160 agg aga tac atc ggt agg tac gga ctg gcg cat gtt tcc aag tgg aac      528
Arg Arg Tyr Ile Gly Arg Tyr Gly Leu Ala His Val Ser Lys Trp Asn
                165                 170                 175 ttc gag acg tgg aat gag cca gac cac cac gac ttt gac aac gtc tcc      576
Phe Glu Thr Trp Asn Glu Pro Asp His His Asp Phe Asp Asn Val Ser
            180                 185                 190 atg acc atg caa ggc ttc ctg aac tac tac gat gcc tgc tcg gag ggt      624
Met Thr Met Gln Gly Phe Leu Asn Tyr Tyr Asp Ala Cys Ser Glu Gly
        195                 200                 205 ctg cgc gcc gcc agc ccc gcc ctg cgg ctg gga ggc ccc ggc gac tcc      672
Leu Arg Ala Ala Ser Pro Ala Leu Arg Leu Gly Gly Pro Gly Asp Ser
210                 215                 220 ttc cac acc cca ccg cga tcc ccg ctg agc tgg ggc ctc ctg cgc cac      720
Phe His Thr Pro Pro Arg Ser Pro Leu Ser Trp Gly Leu Leu Arg His
225                 230                 235                 240 tgc cac gac ggt acc aac ttc ttc act ggg gag gcg ggc gtg cgg ctg      768
Cys His Asp Gly Thr Asn Phe Phe Thr Gly Glu Ala Gly Val Arg Leu
                245                 250                 255 gac tac atc tcc ctc cac agg aag ggt gcg cgc agc tcc atc tcc atc      816
Asp Tyr Ile Ser Leu His Arg Lys Gly Ala Arg Ser Ser Ile Ser Ile
            260                 265                 270 ctg gag cag gag aag gtc gtc gcg cag cag atc cgg cag ctc ttc ccc      864
Leu Glu Gln Glu Lys Val Val Ala Gln Gln Ile Arg Gln Leu Phe Pro
        275                 280                 285 aag ttc gcg gac acc ccc att tac aac gac gag gcg gac ccg ctg gtg      912
Lys Phe Ala Asp Thr Pro Ile Tyr Asn Asp Glu Ala Asp Pro Leu Val
    290                 295                 300 ggc tgg tcc ctg cca cag ccg tgg agg gcg gac gtg acc tac gcg gcc      960
Gly Trp Ser Leu Pro Gln Pro Trp Arg Ala Asp Val Thr Tyr Ala Ala
305                 310                 315                 320 atg gtg gtg aag gtc atc gcg cag cat cag aac ctg cta ctg gcc aac     1008
Met Val Val Lys Val Ile Ala Gln His Gln Asn Leu Leu Leu Ala Asn
                325                 330                 335 acc acc tcc gcc ttc ccc tac gcg ctc ctg agc aac gac aat gcc ttc     1056
Thr Thr Ser Ala Phe Pro Tyr Ala Leu Leu Ser Asn Asp Asn Ala Phe
            340                 345                 350 ctg agc tac cac ccg cac ccc ttc gcg cag cgc acg ctc acc gcg cgc     1104
Leu Ser Tyr His Pro His Pro Phe Ala Gln Arg Thr Leu Thr Ala Arg
        355                 360                 365 ttc cag gtc aac aac acc cgc ccg ccg cac gtg cag ctg ttg cgc aag     1152
Phe Gln Val Asn Asn Thr Arg Pro Pro His Val Gln Leu Leu Arg Lys
    370                 375                 380 ccg gtg ctc acg gcc atg ggg ctg ctg gcg ctg ctg gat gag gag cag     1200
Pro Val Leu Thr Ala Met Gly Leu Leu Ala Leu Leu Asp Glu Glu Gln
385                 390                 395                 400 ctc tgg gcc gaa gtg tcg cag gcc ggg acc gtc ctg gac agc aac cac     1248
Leu Trp Ala Glu Val Ser Gln Ala Gly Thr Val Leu Asp Ser Asn His
                405                 410                 415 acg gtg ggc gtc ctg gcc agc gcc cac cgc ccc cag ggc ccg gcc gac     1296
Thr Val Gly Val Leu Ala Ser Ala His Arg Pro Gln Gly Pro Ala Asp
            420                 425                 430 gcc tgg cgc gcc gcg gtg ctg atc tac gcg agc gac gac acc cgc gcc     1344
Ala Trp Arg Ala Ala Val Leu Ile Tyr Ala Ser Asp Asp Thr Arg Ala
        435                 440                 445
```

```
cac ccc aac cgc agc gtc gcg gtg acc ctg cgg ctg cgc ggg gtg ccc         1392
His Pro Asn Arg Ser Val Ala Val Thr Leu Arg Leu Arg Gly Val Pro
    450             455                 460 ccc ggc ccg ggc ctg gtc tac gtc acg cgc tac ctg gac aac ggg ctc         1440
Pro Gly Pro Gly Leu Val Tyr Val Thr Arg Tyr Leu Asp Asn Gly Leu
465             470                 475                 480 tgc agc ccc gac ggc gag tgg cgg cgc ctg ggc cgg ccc gtc ttc ccc         1488
Cys Ser Pro Asp Gly Glu Trp Arg Arg Leu Gly Arg Pro Val Phe Pro
                485                 490                 495 acg gca gag cag ttc cgg cgc atg cgc gcg gct gag gac ccg gtg gcc         1536
Thr Ala Glu Gln Phe Arg Arg Met Arg Ala Ala Glu Asp Pro Val Ala
            500                 505                 510 gcg gcg ccc cgc ccc tta ccc gcc ggc ggc cgc ctg acc ctg cgc ccc         1584
Ala Ala Pro Arg Pro Leu Pro Ala Gly Gly Arg Leu Thr Leu Arg Pro
        515                 520                 525 gcg ctg cgg ctg ccg tcg ctt ttg ctg gtg cac gtg tgt gcg cgc ccc         1632
Ala Leu Arg Leu Pro Ser Leu Leu Leu Val His Val Cys Ala Arg Pro
    530                 535                 540 gag aag ccg ccc ggg cag gtc acg cgg ctc cgc gcc ctg ccc ctg acc         1680
Glu Lys Pro Pro Gly Gln Val Thr Arg Leu Arg Ala Leu Pro Leu Thr
545             550                 555                 560 caa ggg cag ctg gtt ctg gtc tgg tcg gat gaa cac gtg ggc tcc aag         1728
Gln Gly Gln Leu Val Leu Val Trp Ser Asp Glu His Val Gly Ser Lys
                565                 570                 575 tgc ctg tgg aca tac gag atc cag ttc tct cag gac ggt aag gcg tac         1776
Cys Leu Trp Thr Tyr Glu Ile Gln Phe Ser Gln Asp Gly Lys Ala Tyr
            580                 585                 590 acc ccg gtc agc agg aag cca tcg acc ttc aac ctc ttt gtg ttc agc         1824
Thr Pro Val Ser Arg Lys Pro Ser Thr Phe Asn Leu Phe Val Phe Ser
        595                 600                 605 cca gac aca ggt gct gtc tct ggc tcc tac cga gtt cga gcc ctg gac         1872
Pro Asp Thr Gly Ala Val Ser Gly Ser Tyr Arg Val Arg Ala Leu Asp
    610                 615                 620 tac tgg gcc cga cca ggc ccc ttc tcg gac cct gtg ccg tac ctg gag         1920
Tyr Trp Ala Arg Pro Gly Pro Phe Ser Asp Pro Val Pro Tyr Leu Glu
625             630                 635                 640 gtc cct gtg cca aga ggg ccc cca tcc ccg ggc aat cca tga             1962
Val Pro Val Pro Arg Gly Pro Pro Ser Pro Gly Asn Pro
                645                 650

<210> SEQ ID NO 4
<211> LENGTH: 653
<212> TYPE: PRT
<213> ORGANISM: Homo sapiens

<400> SEQUENCE: 4

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
                20                  25                  30

His Val Asp Ala Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
        50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95
```

Val Thr Thr Arg Gly Ser Thr Gly Arg Gly Leu Ser Tyr Asn Phe Thr
            100                 105                 110

His Leu Asp Gly Tyr Leu Asp Leu Arg Glu Asn Gln Leu Leu Pro
        115                 120                 125

Gly Phe Glu Leu Met Gly Ser Ala Ser Gly His Phe Thr Asp Phe Glu
        130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
        290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
        370                 375                 380

Pro Val Leu Thr Ala Met Gly Leu Leu Ala Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
        450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro

-continued

```
              515                 520                 525
Ala Leu Arg Leu Pro Ser Leu Leu Val His Val Cys Ala Arg Pro
        530                 535             540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585             590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
        610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

ENGINEERED ENZYME FOR ENZYME REPLACEMENT THERAPY

CROSS REFERENCE TO RELATED APPLICATIONS

This application is the National Stage of International Application No. PCT/US2016/045715, filed on Aug. 5, 2016, which claims priority to U.S. Provisional Application No. 62/201,889, filed on Aug. 6, 2015. The contents of both applications are hereby incorporated herein by reference in their entirety.

BACKGROUND

Lysosomal storage disorders (LSDs) include over 50 different diseases with a wide range of clinical phenotypes and a combined incidence of 1 in 7000 live births. LSDs are each caused by a genetic deficiency of lysosomal enzymes, resulting in the accumulation of unprocessed glycosaminoglycans (GAG) and progressive tissue damage. Enzyme replacement therapy (ERT) provides an effective treatment for many LSDs and is approved by the US Food and Drug Administration for treatment of mucopolysaccharidosis (MPS) type I, II, IV, type I Gaucher, and Fabry diseases. ERT involves intravenous injection of therapeutic enzymes to replenish absent or defective enzymes and thus clear accumulating metabolites.

Administration of recombinant enzymes can induce immune responses in patients that lack or possess truncated endogenous enzymes. In fact, antibodies against therapeutic enzymes are found in the serum of ERT patients with frequencies ranging from 15% for Gaucher, 55-80% for Fabry, 91% for MPS I, 97% for MPS IV, and 100% for Pompe disease. There is increasing evidence that antibody responses in patients can hinder ERT efficacy. For example, in Pompe disease, there are clear relationships between protein levels, antibody responses, and therapeutic outcomes. Patients with complete absence of acid alpha-glucosidase were found to have high antibody titers against this enzyme and show inhibition of enzyme uptake and activity during ERT. Other studies also suggest similar results in Fabry and Pompe diseases. In a MPS I animal model, it was also reported that α-L-iduronidase specific antibodies reduce ERT therapeutic efficacy. Induction of immune-tolerance by treatment of patients with immunosuppressive drugs was shown to increase tissue enzyme levels and reduce GAG levels in said patients. Antibody mediated inhibition of enzyme uptake in MPS I patients also strongly correlated to poorer biomarker responses which may suggest an important role in clinical outcomes. Life-threatening anaphylactic reactions have also occurred in patients receiving a recombinant human alpha-iduronidase, laronidase. These studies highlight the importance of maintaining minimal immune responses against recombinant enzymes in ERT clinical use.

LSDs are usually heterogeneous in individual patients and thus a universal deimmunization method such as removing immunogenic epitopes of the therapeutic protein is difficult to achieve. Current strategies to overcome the antibody responses to recombinant enzymes are largely focused on inducing immune tolerance. However, this may be harmful to patients because the regimen is usually coupled with high doses of immunosuppressive drugs. Increased risk of infection and malignancy are also of concern.

SUMMARY

In one aspect, described herein is an engineered enzyme that includes an amino acid sequence that is at least 80% identical to the amino acid sequence of a human beta-glucuronidase, wherein the engineered enzyme exhibits a higher level of alpha-iduronidase enzymatic activity as compared to that of the human beta-glucuronidase.

In one embodiment, the human beta-glucuronidase has the amino acid sequence of SEQ ID NO:2 and the engineered enzyme can have a substitution at at least one residue that corresponds to residue T204, Q279, K438, N484, N502, S503, Y504, S506, Y508, H509, G542, T545, L565, W587, F592, T594, E595, P598, R600, G603, N604, K606, or P636 in the sequence of SEQ ID NO:2. For example, the engineered enzyme can have residues S484, D502, A503, G506, A509, D542, A545, Y592, V595, S604, and/or F606. In another example, the engineered enzyme has residues H279, C484, K502, Y503, G504, G506, P509, A545, A565, L594, Q595, A604, and/or F606. Alternatively, the engineered enzyme can have residues D484, K502, Y503, G506, D508, P509, A545, Y592, L594, G595, D598, T604, F606, and/or 5636. The engineered enzyme can be used to treat a subject having a disorder associated with a deficient enzyme, such as a subject having mucopolysaccharidosis.

In another aspect, described herein is a method of developing a candidate enzyme replacement therapy for treating a disorder associated with a deficient enzyme in a subject having the disorder. The method includes selecting a template enzyme, wherein the template enzyme is endogenous and/or non-immunogenic to the subject and expressed normally in the subject, and altering the template enzyme to obtain an engineered enzyme, wherein the engineered enzyme exhibits an increased target enzymatic activity as compared to that of the template enzyme, the target enzymatic activity being an enzymatic activity of the wild-type counterpart of the deficient enzyme; wherein the engineered enzyme is a candidate enzyme replacement therapy for treating the disorder.

The details of one or more embodiments are set forth in the accompanying drawing and the description below. Other features, objects, and advantages of the embodiments will be apparent from the description and drawing, and from the claims.

DETAILED DESCRIPTION

Figure 1:
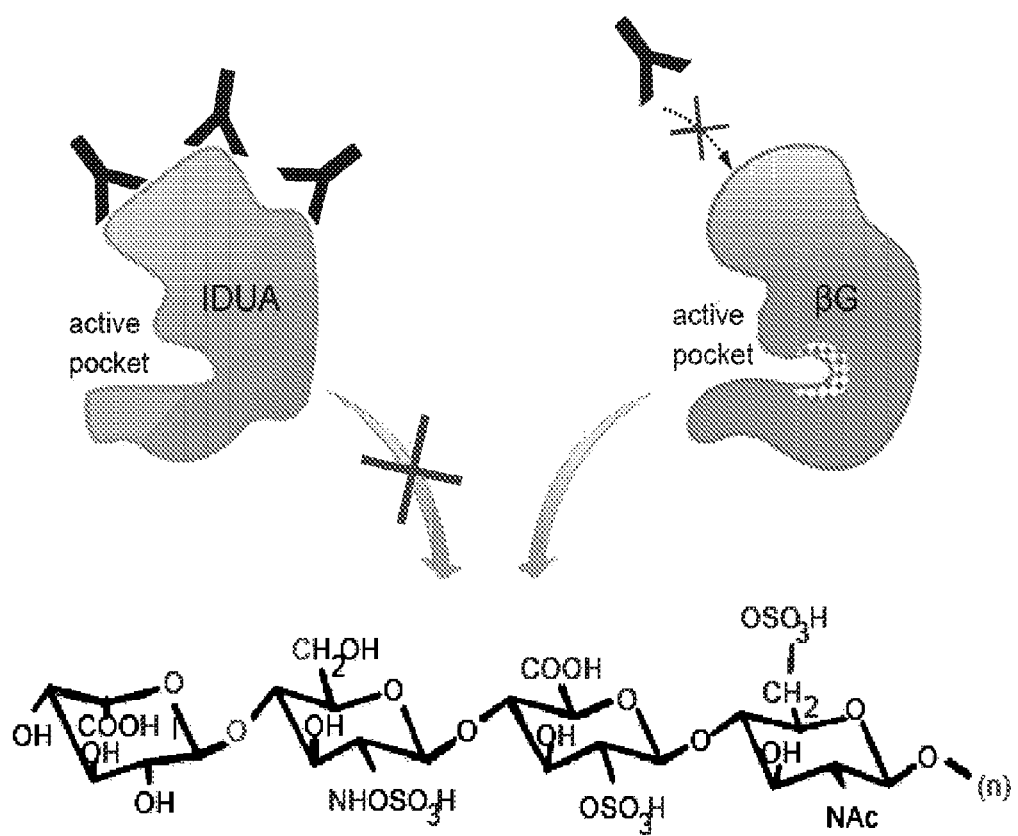
FIG. 1 is an illustration of the concept of "cloaked stealth" enzyme for enzyme replacement therapy. Wild-type alpha-iduronidase (IDUA) can generate specific antibodies in mucopolysaccharidosis (MPS) type I patients which can inhibit the therapeutic efficacy and even cause life-threatening anaphylactic reactions. Beta-glucuronidase (βG) variants which have been altered in their active pockets to display alpha-iduronidase activity may appear as normal immunotolerant self-proteins and thus be able to prevent and/or minimize antibody responses, thereby retaining therapeutic activity and reducing side effects. The sizes of human immunoglobulin G (150 kDa), alpha-iduronidase (83 kDa), and beta-glucuronidase (78 kDa) are not drawn to scale.

Described herein are engineered enzymes useful for enzyme replacement therapies and methods of developing an enzyme replacement therapy.

It was discovered that the enzymatic activity or specificity of a template enzyme can be at least partially switched to that of another enzyme without dramatic alterations in the structure or sequence of the template enzyme.

Hence, described herein is an engineered enzyme, generated from a human beta-glucuronidase template (e.g., a wild-type beta-glucuronidase), that exhibits a higher level of alpha-iduronidase enzymatic activity than the template human beta-glucuronidase. The engineered enzyme shares high amino acid sequence identity (e.g., at least 80%, 85%, 90%, 95%, 97% or 99%) with the template beta-glucuronidase but very low sequence identity with a human alpha-iduronidase.

Exemplary nucleic acid and amino acid sequences of human beta-glucuronidase and human alpha-iduronidase are provided below.

```
A human beta-glucuronidase nucleic acid sequence
(SEQ ID NO: 1):
ATGGCCCGGGGTCGGCGGTTGCCTGGGCGGCGCTCGGGCCGTTGTTGTG
GGGCTGCGCGCTGGGGCTGCAGGGCGGGATGCTGTACCCCCAGGAGAGCC
CGTCGCGGGAGTGCAAGGAGCTGGACGGCCTCTGGAGCTTCCGCGCCGAC
TTCTCTGACAACCGACGCCGGGGCTTCGAGGAGCAGTGGTACCGGCGGCC
GCTGTGGGAGTCAGGCCCCACCGTGGACATGCCAGTTCCCTCCAGCTTCA
ATGACATCAGCCAGGACTGGCGTCTGCGGCATTTTGTCGGCTGGGTGTGG
TACGAACGGGAGGTGATCCTGCCGGAGCGATGGACCCAGGACCTGCGCAC
AAGAGTGGTGCTGAGGATTGGCAGTGCCCATTCCTATGCCATCGTGTGGG
TGAATGGGGTCGACACGCTAGAGCATGAGGGGGGCTACCTCCCCTTCGAG
GCCGACATCAGCAACCTGGTCCAGGTGGGGCCCCTGCCCTCCCGGCTCCG
AATCACTATCGCCATCAACAACACACTCACCCCCACCACCCTGCCACCAG
GGACCATCCAATACCTGACTGACACCTCCAAGTATCCCAAGGGTTACTTT
GTCCAGAACACATATTTTGACTTTTTCAACTACGCTGGACTGCAGCGGTC
TGTACTTCTGTACACGACACCCACCACCTACATCGATGACATCACCGTCA
CCACCAGCGTGGAGCAAGACAGTGGGCTGGTGAATTACCAGATCTCTGTC
AAGGGCAGTAACCTGTTCAAGTTGGAAGTGCGTCTTTTGGATGCAGAAAA
CAAAGTCGTGGCGAATGGGACTGGGACCCAGGGCCAACTTAAGGTGCCAG
GTGTCAGCCTCTGGTGGCCGTACCTGATGCACGAACGCCCTGCCTATCTG
TATTCATTGGAGGTGCAGCTGACTGCACAGACGTCACTGGGGCCTGTGTC
TGACTTCTACACACTCCCTGTGGGGATCCGCACTGTGGCTGTCACCAAGA
GCCAGTTCCTCATCAATGGGAAACCTTTCTATTTCCACGGTGTCAACAAG
CATGAGGATGCGGACATCCGAGGGAAGGGCTTCGACTGGCCGCTGCTGGT
GAAGGACTTCAACCTGCTTCGCTGGCTTGGTGCCAACGCTTTCCGTACCA
GCCACTACCCCTATGCAGAGGAAGTGATGCAGATGTGTGACCGCTATGGG
ATTGTGGTCATCGATGAGTGTCCCGGCGTGGGCCTGGCGCTGCCGCAGTT
CTTCAACAACGTTTCTCTGCATCACCACATGCAGGTGATGGAAGAAGTGG
TGCGTAGGGACAAGAACCACCCCGCGGTCGTGATGTGGTCTGTGGCCAAC
GAGCCTGCGTCCCACCTAGAATCTGCTGGCTACTACTTGAAGATGGTGAT
CGCTCACACCAAATCCTTGGACCCCTCCCGGCCTGTGACCTTTGTGAGCA
ACTCTAACTATGCAGCAGACAAGGGGGCTCCGTATGTGGATGTGATCTGT
TTGAACAGCTACTACTCTTGGTATCACGACTACGGGCACCTGGAGTTGAT
TCAGCTGCAGCTGGCCACCCAGTTTGAGAACTGGTATAAGAAGTATCAGA
AGCCCATTATTCAGAGCGAGTATGGAGCAGAAACGATTGCAGGGTTTCAC
CAGGATCCACCTCTGATGTTCACTGAAGAGTACCAGAAAAGTCTGCTAGA
GCAGTACCATCTGGGTCTGGATCAAAAACGCAGAAAATACGTGGTTGGAG
AGCTCATTTGGAATTTTGCCGATTTCATGACTGAACAGTCACCGACAGAG
GTGCTGGGGAATAAAAAGGGGATCTTCACTCGGCAGAGACAACCAAAAAG
TGCAGCGTTCCTTTTGCGAGAGAGATACTGGAAGATTGCCAATGAAACCA
GGTATCCCCACTCAGTAGCCAAGTCACAATGTTTGGAAAACAGCCTGTTT
ACTTGA A human beta-glucuronidase amino acid sequence
                              (SEQ ID NO: 2)
MARGSAVAWAALGPLLWGCALGLQGGMLYPQESPSRECKELDGLWSFRAD
FSDNRRRGFEEQWYRRPLWESGPTVDMPVPSSFNDISQDWRLRHFVGWVW
YEREVILPERWTQDLRTRVVLRIGSAHSYAIVWVNGVDTLEHEGGYLPFE
ADISNLVQVGPLPSRLRITIAINNTLTPTTLPPGTIQYLTDTSKYPKGYF
VQNTYFDFFNYAGLQRSVLLYTTPTTYIDDITVTTSVEQDSGLVNYQISV
KGSNLFKLEVRLLDAENKVVANGTGTQGQLKVPGVSLWWPYLMHERPAYL
YSLEVQLTAQTSLGPVSDFYTLPVGIRTVAVTKSQFLINGKPFYFHGVNK
HEDADIRGKGFDWPLLVKDFNLLRWLGANAFRTSHYPYAEEVMQMCDRYG
IVVIDECPGVGLALPQFFNNVSLHHHMQVMEEVVRRDKNHPAVVMWSVAN
EPASHLESAGYYLKMVIAHTKSLDPSRPVTFVSNSNYAADKGAPYVDVIC
LNSYYSWYHDYGHLELIQLQLATQFENWYKKYQKPIIQSEYGAETIAGFH
QDPPLMFTEEYQKSLLEQYHLGLDQKRRKYVVGELIWNFADFMTEQSPIR
VLGNKKGIFTRQRQPKSAAFLLRERYWKIANETRYPHSVAKSQCLENSLF
T A human alpha-iduronidase nucleic acid sequence
                              (SEQ ID NO: 3)
ATGCGTCCCCTGCGCCCCCGCGCCGCGCTGCTGGCGCTCCTGGCCTCGCT
CCTGGCCGCGCCCCCGGTGGCCCCGGCCGAGGCCCCCGCACCTGGTGCATG
TGGACGCGGCCCGCGCGCTGTGGCCCCTGCGGCGCTTCTGGAGGAGCACA
GGCTTCTGCCCCCGCTGCCACACAGCCAGGCTGACCAGTACGTCCTCAG
CTGGGACCAGCAGCTCAACCTCGCCTATGTGGGCGCCGTCCCTCACCGCG
GCATCAAGCAGGTCCGGACCCACTGGCTGCTGGAGCTTGTCACCACCAGG
GGGTCCACTGGACGGGGCCTGAGCTACAACTTCACCCACCTGGACGGGTA
CCTGGACCTTCTCAGGGAGAACCAGCTCCTCCCAGGGTTTGAGCTGATGG
GCAGCGCCTCGGGCCACTTCACTGACTTTGAGGACAAGCAGCAGGTGTTT
GAGTGGAAGGACTTGGTCTCCAGCCTGGCCAGGAGATACATCGGTAGGTA
CGGACTGGCGCATGTTTCCAAGTGGAACTTCGAGACGTGGAATGAGCCAG
ACCACCACGACTTTGACAACGTCTCCATGACCATGCAAGGCTTCCTGAAC
TACTACGATGCCTGCTCGGAGGGTCTGCGCGCCGCCAGCCCCGCCCTGCG
GCTGGGAGGCCCCGGCGACTCCTTCCACACCCCACCGCGATCCCCGCTGA
GCTGGGCCTCCTGCGCCACTGCCACGACGGTACCAACTTCTTCACTGGG
GAGGCGGGCGTGCGGCTGGACTACATCTCCCTCCACAGGAAGGGTGCGCG
CAGCTCCATCTCCATCCTGGAGCAGGAGAAGGTCGTCGCGCAGCAGATCC
GGCAGCTCTTCCCCAAGTTCGCGGACACCCCCATTTACAACGACGAGGCG
GACCCGCTGGTGGGCTGGTCCCTGCCACAGCCGTGGAGGGCGGACGTGAC
CTACGCGGCCATGGTGGTGAAGGTCATCGCGCAGCATCAGAACCTGCTAC
TGGCCAACACCACCTCCGCCTTCCCCTACGCGCTCCTGAGCAACGACAAT
GCCTTCCTGAGCTACCACCCGCACCCCTTCGCGCAGCGCACGCTCACCGC
```

-continued

```
GCGCTTCCAGGTCAACAACACCCGCCCGCCGCACGTGCAGCTGTTGCGCA

AGCCGGTGCTCACGGCCATGGGGCTGCTGGCGCTGCTGGATGAGGAGCAG

CTCTGGGCCGAAGTGTCGCAGGCCGGGACCGTCCTGGACAGCAACCACAC

GGTGGGCGTCCTGGCCAGCGCCCACCGCCCCCAGGGCCCGGCCGACGCCT

GGCGCGCCGCGGTGCTGATCTACGCGAGCGACGACACCCGCGCCCACCCC

AACCGCAGCGTCGCGGTGACCCTGCGGCTGCGCGGGGTGCCCCCCGGCCC

GGGCCTGGTCTACGTCACGCGCTACCTGGACAACGGGCTCTGCAGCCCCG

ACGGCGAGTGGCGGCGCCTGGGCCGGCCCGTCTTCCCCACGGCAGAGCAG

TTCCGGCGCATGCGCGCGGCTGAGGACCCGGTGGCCGCGGCGCCCCGCCC

CTTACCCGCCGGCGGCCGCCTGACCCTGCGCCCCGCGCTGCGGCTGCCGT

CGCTTTTGCTGGTGCACGTGTGTGCGCGCCCCGAGAAGCCGCCCGGGCAG

GTCACGCGGCTCCGCGCCCTGCCCCTGACCCAAGGGCAGCTGGTTCTGGT

CTGGTCGGATGAACACGTGGGCTCCAAGTGCCTGTGGACATACGAGATCC

AGTTCTCTCAGGACGGTAAGGCGTACACCCCGGTCAGCAGGAAGCCATCG

ACCTTCAACCTCTTTGTGTTCAGCCCAGACACAGGTGCTGTCTCTGGCTC

CTACCGAGTTCGAGCCCTGGACTACTGGGCCCGACCAGGCCCCTTCTCGG

ACCCTGTGCCGTACCTGGAGGTCCCTGTGCCAAGAGGGCCCCCATCCCCG

GGCAATCCATGA
```

A human alpha-iduronidase amino acid sequence
(SEQ ID NO: 4)
MRPLRPRAALLALLASLLAAPPVAPAEAPHLVHVDAARALWPLRRFWRST

GFCPPLPHSQADQYVLSWDQQLNLAYVGAVPHRGIKQVRTHWLLELVTTR

GSTGRGLSYNFTHLDGYLDLLRENQLLPGFELMGSASGHFTDFEDKQQVF

EWKDLVSSLARRYIGRYGLAHVSKWNFETWNEPDHHDFDNVSMTMQGFLN

YYDACSEGLRAASPALRLGGPGDSFHTPPRSPLSWGLLRHCHDGTNFFTG

EAGVRLDYISLHRKGARSSISILEQEKVVAQQIRQLFPKFADTPIYNDEA

DPLVGWSLPQPWRADVTYAAMVVKVIAQHQNLLLANTTSAFPYALLSNDN

AFLSYHPHPFAQRTLTARFQVNNTRPPHVQLLRKPVLTAMGLLALLDEEQ

LWAEVSQAGTVLDSNHTVGVLASAHRPQGPADAWRAAVLIYASDDTRAHP

NRSVAVTLRLRGVPPGPGLVYVTRYLDNGLCSPDGEWRRLGRPVFPTAEQ

FRRMRAAEDPVAAAPRPLPAGGRLTLRPALRLPSLLLVHVCARPEKPPGQ

VTRLRALPLTQGQLVLVWSDEHVGSKCLWTYEIQFSQDGKAYTPVSRKPS

TFNLFVFSPDTGAVSGSYRVRALDYWARPGPFSDPVPYLEVPVPRGPPSP

GNP

The engineered enzyme can have an amino acid sequence that is at least 80% identical to the sequence of SEQ ID NO:2 and include amino acid substitution(s) at one or more position(s) corresponding to the group of position(s) in the sequence of SEQ ID NO:2 (e.g., as determined by a sequence alignment) consisting of: 204, 279, 438, 484, 502, 503, 504, 506, 508, 509, 542, 545, 565, 587, 592, 594, 595, 598, 600, 603, 604, 606 and 636. For example, the engineered enzyme can have, at one or more of said above-mentioned 23 positions, the corresponding wild-type residue (as set forth in SEQ ID NO:2), or any other amino acid (e.g., A, R, N, D, C, E, Q, G, H, I, L, K, M, F, P, S, T, W, Y, V, or an analog thereof).

In one embodiment, said engineered enzyme have an amino acid sequence that is at least 80%, 85%, 90%, 95%, 97% or 99% identical to the sequence as set forth in SEQ ID NO:2.

In one embodiment, the engineered enzyme has an amino acid sequence in which, as compared to the sequence of SEQ ID NO:2, corresponding position 204 is T or K; position 279 is Q or H; position 438 is K or M; position 484 is S, D, H, R, or C; position 502 is N, D, or K; position 503 is A, D, Y, P, or V; position 504 is Y, G, or C; position 506 is S or G; position 508 is Y or D; position 509 is H, A, or P; position 542 is G or D; position 545 is T or A; position 565 is L or A; position 587 is W or T; position 592 is F or Y; position 594 is T or L; position 595 is L, V, Q, or G; position 598 is P or D; position 600 is R or A; position 603 is G or E; position 604 is Y, S, A, or T; position 606 is Q, F, or L; and position 636 is P or S. In one embodiment, substitution of amino acid residue(s) of the engineered enzyme amino acids was carried out as according to Table 1 or Table 2 (see below).

For example, the engineered enzyme can have, as compared to the sequence of SEQ ID NO:2, the following altered/substituted residue(s): S484, D502, A503, G506, A509, D542, A545, Y592, V595, S604, and/or F606. Another exemplary engineered enzyme has the following altered residues: H279, C484, K502, Y503, G504, G506, P509, A545, A565, L594, Q595, A604, and/or F606. Yet another engineered enzyme can have the following altered residues: D484, K502, Y503, G506, D508, P509, A545, Y592, L594, G595, D598, T604, F606, and/or S636.

Certain residues in a wild-type human beta-glucuronidase (e.g., SEQ ID NO:2) may be particular targets for altering its enzymatic activity, e.g., N484, N502, S503, S506, H509, F592, E595, N604, and K606. Hence, in one embodiment the engineered enzyme can include amino acid substitution(s) at one or more of said nine amino acid positions. On the other hand, certain wild-type residues, e.g., S447, G542, L565, W587, R600, G603, and P636, may be preferred. The engineered enzyme can thus retain one or more of these seven wild-type residues (as set forth in SEQ ID NO:2). As such, in one embodiment, the engineered enzyme does not have a substitution at a residue that corresponds to residue S447, G542, L565, W587, R600, G603, and/or P636 of the sequence of SEQ ID NO:2.

In one embodiment, the present invention also provides an isolated polynucleotide encoding the engineered enzyme as described herein.

In another embodiment, the present invention provides an expression vector comprising said polynucleotide encoding the engineered enzyme as described herein.

Methods known in the art, e.g., recombinant techniques, can be employed to generate the engineered enzyme described herein.

The engineered enzyme can be used as an enzyme replacement therapy to treat a subject having a disorder associated with a defective alpha-iduronidase, i.e., mucopolysaccharidosis. As the engineered enzyme will appear to the immune system of the subject as a normal, non-immunogenic endogenous enzyme, it will not induce unwanted immune responses in the subject.

Gene therapy involving administration of a nucleic acid molecule encoding the engineered enzyme can also be used to treat mucopolysaccharidosis in a subject.

Also described herein is a method of developing or identifying a candidate enzyme replacement therapy for treating a disorder associated with a deficient enzyme in a subject having the disorder, e.g., a lysosomal storage disorder such as MPS type I, MPS II, MPS type IV, type I Gaucher, Pompe disease or Fabry disease. The deficiency can be due to a mutant enzyme (e.g., truncated enzyme) or a lower than normal level of a wild-type enzyme.

In the method, the enzymatic activity and/or specificity of a normal endogenous enzyme (i.e., a template enzyme) are altered to compensate for that of the defective enzyme. As the modified enzyme will appear as a normal endogenous protein, the modified enzyme will not be immunogenic in the subject.

A suitable template enzyme should be one that is endogenous to and expressed normally in a subject having the defective enzyme. The template enzyme and the wild-type counterpart of the defective enzyme can be similar in one or more aspects, e.g., catalytic mechanism, catalytic domain structure, tissue expression profile, size, and cellular localization.

The selected template enzyme is then altered in order to at least partially switch its enzymatic activity or specificity to that of the normal counterpart of the defective enzyme. Such alterations include amino acid substitutions, deletions and insertions. The alterations should not make the template enzyme appear as a foreign protein to the immune system of the subject. In other words, the modified enzyme should still share a high sequence identity (e.g., at least 80%, 85%, 90%, 95%, or 99% identity) with the template enzyme. The alterations can be rationally designed, random, or a combination thereof.

For example, an engineered enzyme can be designed based on the structures (e.g., the structures of the whole enzymes and the structures of the active sites) of the template enzyme and the normal counterpart of the defective enzyme. Various techniques and softwares available in the art can be used to compare the sequences and structures of the two enzymes to identify potential residues for alteration. Residues known or predicted to interact with a substrate may be particular targets for alteration. A library of variants each with substitutions at one or more of the identified residues can be generated for screening. Screening a library of randomly generated variants of the template enzyme can also be carried out to identify variants that exhibit the desired activity and/or specificity.

A candidate enzyme replacement therapy can be further tested (e.g., in an animal model) to determine whether it induces unwanted immune responses. In one embodiment, a candidate enzyme that induces no immune response, or induces a lower level of the immune response as compared to the immune response induced by the deficient enzyme, is selected for enzyme replacement therapy.

The method can be applied to a wild-type human beta-glucuronidase template (e.g., SEQ ID NO:2) to generated engineered enzymes that exhibit an alpha-iduronidase enzymatic activity. Residues within the catalytic domain of human beta-glucuronidase can be altered. As described above, positions 204, 279, 438, 484, 502, 503, 504, 506, 508, 509, 542, 545, 565, 587, 592, 594, 595, 598, 600, 603, 604, 606 and 636 in the sequence of SEQ ID NO:2 are each a target for alteration. Each of the specific engineered enzymes described herein can be further altered (e.g., addition of substituted residues or different substituted residues) to develop more engineered enzymes.

The screening method can be performed using techniques or systems known in the art. An exemplary technique is the Enzyme Cleavable Surface Tethered All-purpose Screen sYstem (ECSTASY). See Chen, C. P., et al., Protein Eng Des Sel, 2012. 25(7): p. 367-75; and also FIG. 2.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, etc. In a preferred embodiment, the subject is a human. In another embodiment, the subject is an experimental animal or animal suitable as a disease model.

The term "treating" as used herein refers to the application or administration of a composition including one or more active agents to a subject, who has a disease, a symptom of the disease, or a predisposition toward the disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are incorporated by reference herein in their entirety.

EXAMPLE

Described below is an alternative strategy in which the enzymatic specificity of a normal endogenous enzyme is altered to compensate for the defective enzyme to help alleviate the antibody response. See FIG. 1. Because the modified enzyme will appear overall as a normal endogenous protein, this enzyme will be less immunogenic in LSD patients.

We employed human beta-glucuronidase as a template to generate alpha-iduronidase analogs. The expression of beta-glucuronidase is normal in MPS I patients, so recombinant beta-glucuronidase should be well tolerated and non-immunogenic. Beta-glucuronidase and alpha-iduronidase share a similar TIM $(\beta/\alpha)8$-barrel structure in their catalytic domains and belong to the same clan of glycoside hydrolase (GH-A). They also have similar catalytic mechanism which hydrolyzes substrates via a pair of glutamic acid residues, E451 and E540 for beta-glucuronidase, and E182 and E299 for alpha-iduronidase in a retentive fashion. In addition, in common with alpha-iduronidase, beta-glucuronidase can be targeted to lysosomes by receptor-mediated endocytosis via mannose-6-phosphate receptors present on the surface of deficient cells. Due to these similarities, beta-glucuronidase was selected as a candidate for specificity switching.

We constructed a beta-glucuronidase library and screened it for alpha-iduronidase activity using the Enzyme Cleavable Surface Tethered All-purpose Screen sYstem (ECSTASY) previously developed in our lab. See FIG. 2 and also Chen, C. P., et al., Protein Eng Des Sel, 2012. 25(7): p. 367-75. The beta-glucuronidase library was surface expressed by fusion to a C-terminal GPI-anchor signal sequence from human decay accelerating factor (DAF). See Caras, I. W., et al., Science, 1987. 238(4831): p. 1280-3. The membrane-bound beta-glucuronidase library cells were screened by high through-put fluorescence-activated cell sorting (FACS) followed by phosphatidylinositol-specific phospholipase C (PI- PLC) cleavage to facilitate screening for alpha-iduronidase activity under defined conditions. After screening, the in vitro effect of the beta-glucuronidase variants in alpha-iduronidase deficient cells was investigated.

We successfully isolated beta-glucuronidase variants that displayed significant alpha-iduronidase activity and exhibited phenotypic effects on MPS I cells. The data demonstrated that the specificity of a normally-expressed endogenous human enzyme can be shifted to compensate for a separate defective enzyme.

Wild-Type Human Beta-Glucuronidase Displays Detectable Alpha-Iduronidase Activity Due to the similarity between human beta-glucuronidase and alpha-iduronidase, we sought to determine if human beta-glucuronidase displayed endogenous alpha-iduronidase activity.

We expressed and purified recombinant human beta-glucuronidase from human alpha-iduronidase deficient fibroblasts derived from MPS type I patients to eliminate possible contamination of the recombinant beta-glucuronidase with endogenous alpha-iduronidase. Recombinant beta-glucuronidase bearing a polyhistidine (6×His) tag was purified by ammonium sulfate precipitation and $Ni^{2+}$-nitrilotriacetic acid affinity chromatography.

Figure 2:
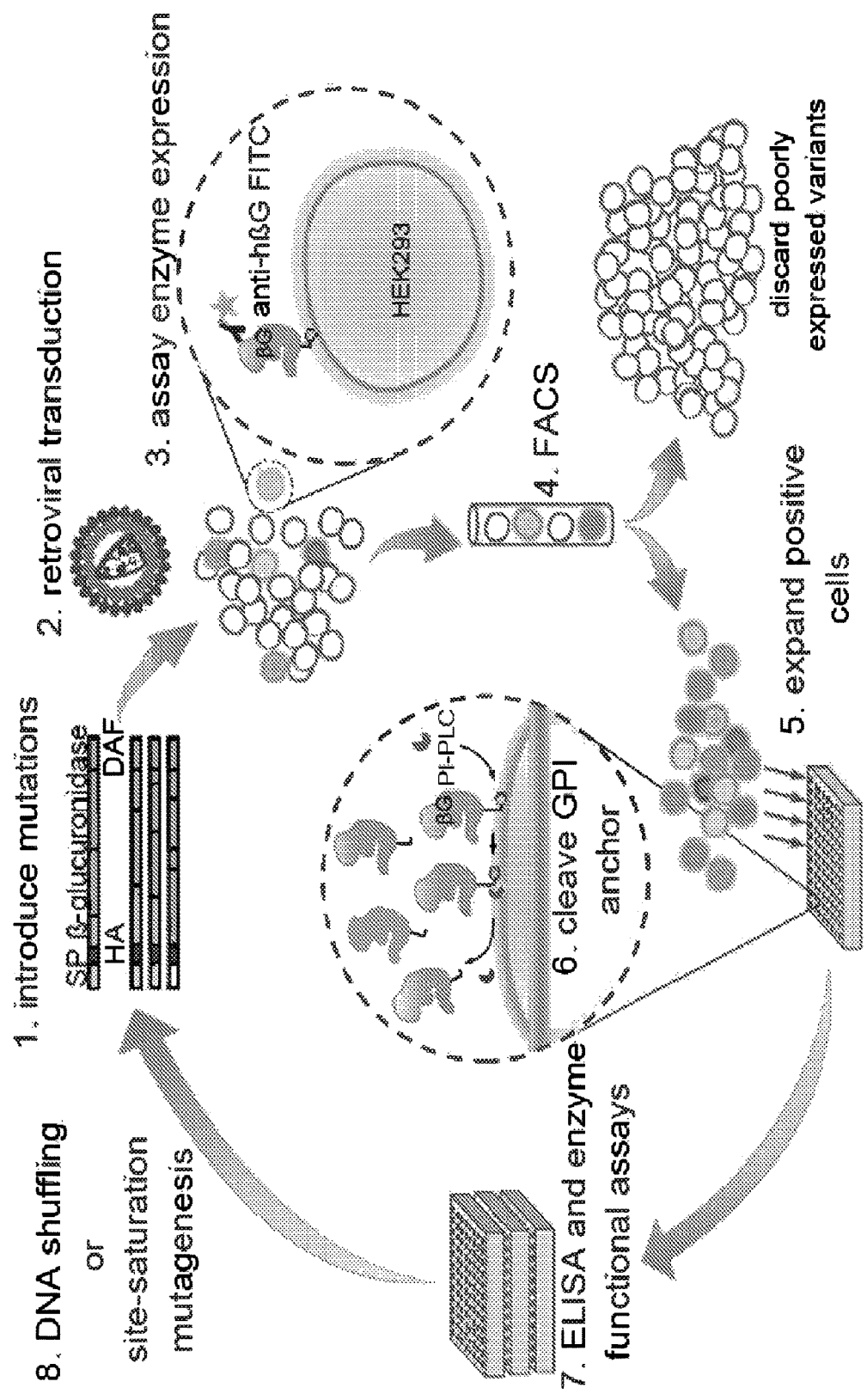
FIG. 2 is an illustration of an application of the enzyme cleavable surface tethered all-purpose screening system (ECSTASY). (1) A library of beta-glucuronidase variants was cloned into a retroviral vector, which codes for a signal peptide, an HA tag, a 6×His tag, an enzyme variant, a myc tag, and the C-terminal 37 amino acids of human DAF. (2) Library cells expressing one GPI-anchored beta-glucuronidase variant each were generated by retroviral transduction of HEK293 cells at a low multiplicity of infection. (3, 4) The cells were immunofluorescence stained with an anti-betaglucuronidase-FITC conjugate to identify cells expressing beta-glucuronidase on their surface. Fluorescence-activated cell sorting was employed to rapidly discard cells expressing misfolded or unstable enzyme variants as determined by low immunofluorescence staining. (5) Positive cells were individually sorted into 96-well microtiter plates and allowed to grow to full confluence. (6) Surface-tethered enzyme variants were released from the cells by PI-PLC cleavage. (7) The supernatant containing soluble enzyme variants were assayed for enzyme concentration by ELISA and enzyme activity by flourometric assays. (8) Selected mutants with higher activity can be used as templates for a new generation library by DNA shuffling or site-saturation mutagenesis.
Figure 3:
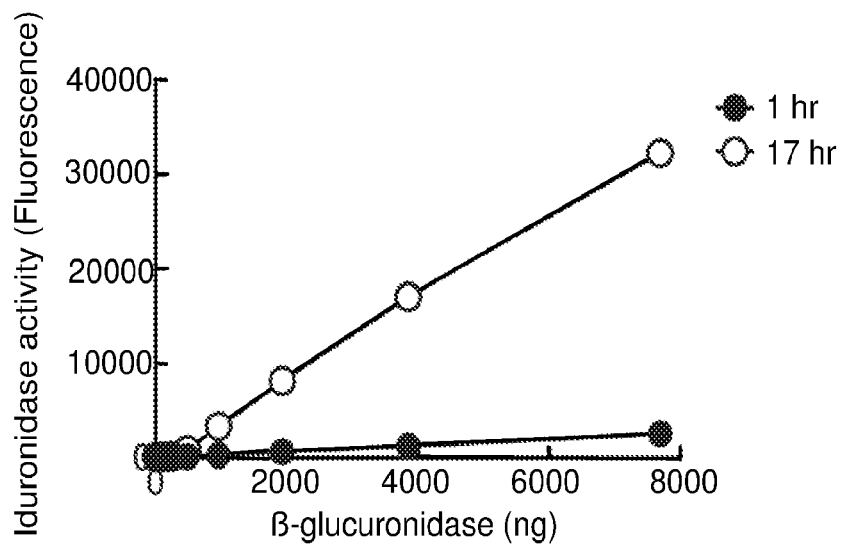
FIG. 3 is a set of graphs showing that human beta-glucuronidase displayed measurable activity toward the alpha-iduronidase substrate MUI. Recombinant human beta-glucuronidase was purified from human alpha-iduronidase deficient cells (34/2000, derived from Mucopolysaccharidosis type I patients) and incubated with 250 μM α-iduronidase substrate 4-methylumbelliferyl alpha-L-iduronide (MUI) in 0.2 M formate buffer, pH 3.5, for 1 or 17 h at 37° C. (A) The fluorescence was detected at an excitation wavelength of 355 nm and an emission wavelength of 460 nm. The hydrolysis of MUI into 4-methylumbelliferone (4-MU) was also detected by solid-phase extraction/high-performance liquid chromatography on a LiChroprep RP18 (40-63 μm) column equilibrated with 20% methanol (pH 4). MUI alone (B) and MUI incubated with human β-glucuronidase (C) was eluted with 25% methanol in double-distilled water (pH 4). Commercial MUI (unpurified) incubated without (D) or with alpha-iduronidase (E) was eluted with 25% methanol in double-distilled water (pH 4).
Figure 3:
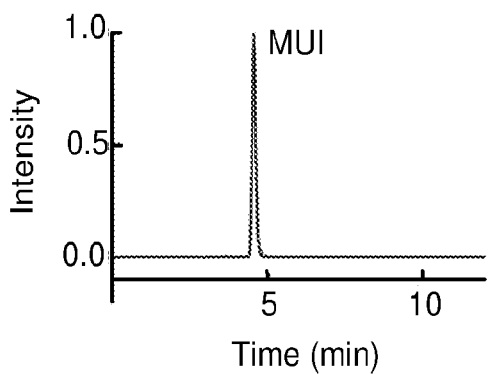
Figure 3:
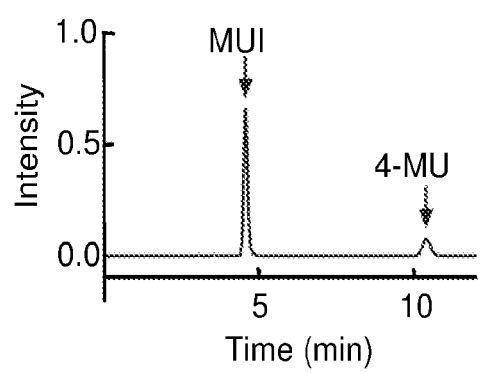
Figure 3:
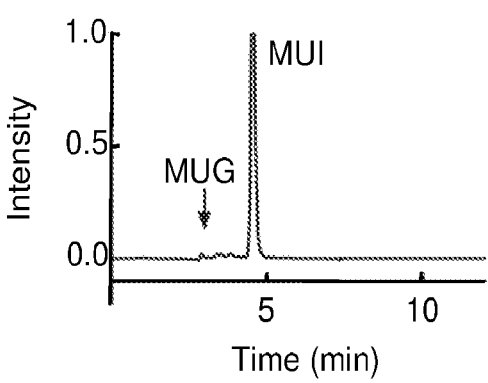
Figure 3:
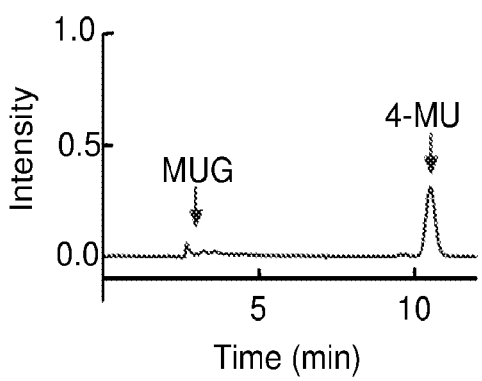

In vitro assay showed that human beta-glucuronidase exhibited measurable activity against the alpha-iduronidase substrate, 4-methylumbelliferyl alpha-L-iduronide (MUI), corresponding to approximately 0.002% of the activity of wild-type human alpha-iduronidase. The hydrolysis of MUI was proportional to human beta-glucuronidase amount and incubation time. See FIG. 3, panel A. This activity was also confirmed by HPLC which showed the hydrolysis of MUI and an increase in the product 4-methylumbelliferone 4-MU. See FIG. 3, panels B and C. Note that commercial MUI contains 4-methylumbelliferyl beta-D-glucuronide (MUG) contamination ranging from 0.1 to 2% as stated in the datasheet provided as well as indicated by HPLC. See FIG. 3, panels D and E. Thus, the commercial MUI was purified as described in Materials and Methods before assaying to avoid signals from hydrolysis of MUG Identification of Human Beta-Glucuronidase Variants Displaying Elevated Alpha-Iduronidase Activity We screened human beta-glucuronidase variants for clones with higher alpha-iduronidase activity by ECSTASY. See FIG. 2. Briefly, a human beta-glucuronidase library with mutations at nineteen residues for a total diversity of $3 \times 10^9$ was designed by structural analysis and literature review. See Table 1.

TABLE 1

Amino acid frequency of beta-glucuronidase variants with high alpha-iduronidase activity (n = 9)

| Position | Expected frequency of each position | WT A.A. | Frequency after ECSTASY Mutant A.A. | | | | | | | |
|---|---|---|---|---|---|---|---|---|---|---|
| 447 | 0.50 | S | E | | | | | | | |
| | | 9 | 0 | | | | | | | |
| | | N | D | H | R | G | S | C | Y | |
| <u>484</u> | 0.125 | 0 | 3 | 1 | 2 | 0 | 2 | 1 | 0 | |
| | | N | E | D | K | | | | | |
| 502 | 0.25 | 2 | 0 | 1 | 6 | | | | | |
| | | S | A | D | Y | P | H | F | L | V |
| <u>503</u> | 0.11 | 0 | 1 | 1 | 4 | 2 | 0 | 0 | 0 | 1 |
| | | Y | G | D | C | | | | | |
| 504 | 0.25 | 4 | 4 | 0 | 1 | | | | | |
| | | S | G | R | | | | | | |
| 506 | 0.33 | 2 | 7 | 0 | | | | | | |
| | | Y | D | | | | | | | |
| 508 | 0.50 | 3 | 5 | | | | | | | |
| | | H | S | D | A | P | Y | | | |
| <u>509</u> | 0.16 | 2 | 0 | 0 | 2 | 5 | 0 | | | |
| | | G | D | | | | | | | |
| 542 | 0.50 | 7 | 2 | | | | | | | |
| | | T | A | | | | | | | |
| 545 | 0.50 | 5 | 4 | | | | | | | |
| | | L | A | | | | | | | |
| 565 | 0.50 | 7 | 2 | | | | | | | |
| | | W | T | | | | | | | |
| 587 | 0.50 | 7 | 2 | | | | | | | |
| | | F | Y | | | | | | | |
| 592 | 0.50 | 2 | 7 | | | | | | | |
| | | T | L | | | | | | | |
| 594 | 0.50 | 6 | 3 | | | | | | | |
| | | E | L | V | Q | G | R | | | |
| <u>595</u> | 0.16 | 0 | 3 | 1 | 1 | 4 | 0 | | | |
| | | P | D | | | | | | | |
| 598 | 0.50 | 3 | 6 | | | | | | | |
| | | R | A | | | | | | | |
| 600 | 0.50 | 7 | 2 | | | | | | | |
| | | N | Y | S | A | T | D | | | |
| <u>604</u> | 0.16 | 0 | 1 | 4 | 1 | 3 | 0 | | | |
| | | K | P | Q | F | L* | | | | |
| <u>606</u> | 0.25 | 0 | 0 | 1 | 7 | 1 | | | | |

Figure 4:
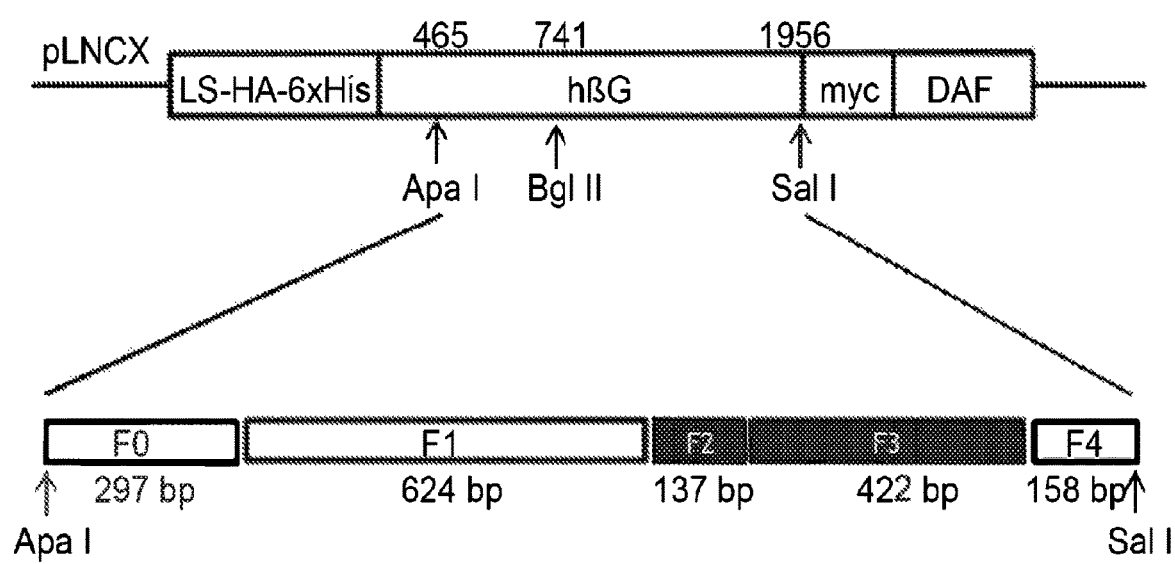
FIG. 4 is an illustration of the construction of a synthetic library. A full-length human beta-glucuronidase variant library was assembled from five DNA fragments (F0-F4) with eighteen overlapping nucleotides between each other. The F0 fragment contains an Apa I cloning site as well as a silent mutation to remove a unique Bgl II cutting site. F2 and F3 fragments, which contain variable amino acids at nineteen positions, were constructed by primer assembly followed by PCR amplification. The F4 fragment contains a Sal I cloning site. All fragments were mixed in equal molar ratios and amplified by PCR to obtain the full-length human beta-glucuronidase library. Wild-type DNA was removed by Bgl II restriction enzyme digestion after library ligation.

Underlined positions are putative hot spots identified from different prediction methods.
*unexpected mutation Mutations were introduced at nineteen positions in the human beta-glucuronidase gene by primer assembly followed by PCR amplification (see FIG. 4), resulting in $1.2 \times 10^7$ bacterial colonies. Retroviral transduction of 293 cells with library DNA at a multiplicity of infection of 0.1 to ensure only a single beta-glucuronidase variant gene in each cell resulted in $3 \times 10^6$ stable clones (293/L1 cells).

Figure 5:
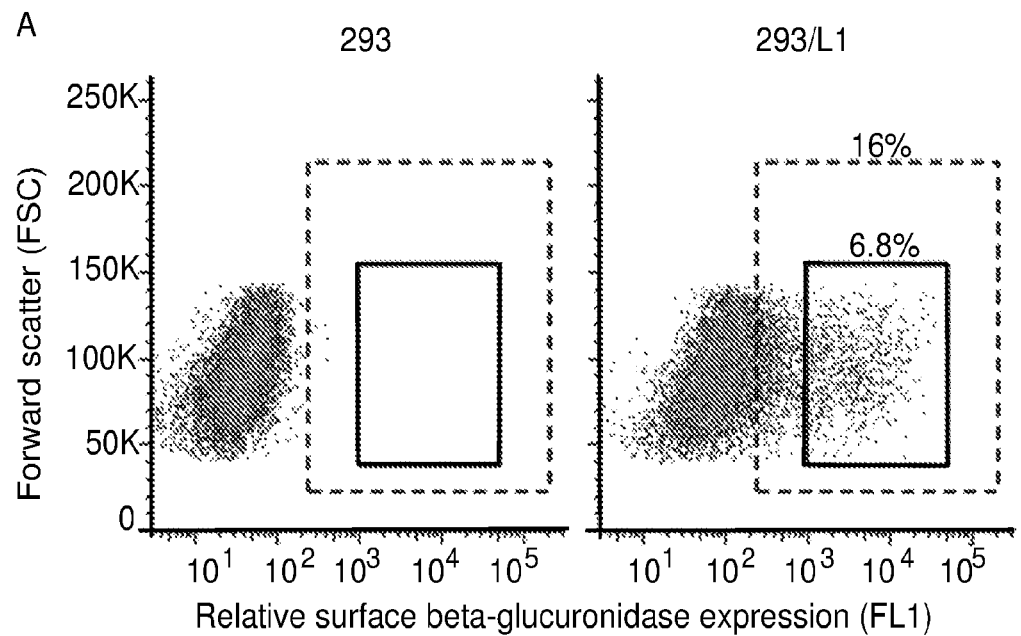
FIG. 5 is a set of graphs showing an example screen of a human beta-glucuronidase synthetic library by ECSTASY. A. 293 and 293/L1 cells were stained with 7G8-FITC and analyzed on a flow cytometer for surface human beta-glucuronidase expression (dashed gate, 16%). Cells exhibiting the highest human beta-glucuronidase expression level (solid gate, 6.8%) were sorted into 96-well microplates as single cells for subsequent screening. B. GPI-anchored human beta-glucuronidase variants were cleaved from individual 293/L1 clones by PI-PLC. The supernatant was assayed for hydrolysis of 4-methylumbelliferyl alpha-L-iduronide (MUI) at pH 3.5. Protein amounts were quantitated by sandwich ELISA. Wild-type and beta-glucuronidase variants are shown as closed and open circles, respectively. C. Specific activity of each beta-glucuronidase variant is presented as relative fluorescence unit (RFU) per ng protein.
Figure 5:
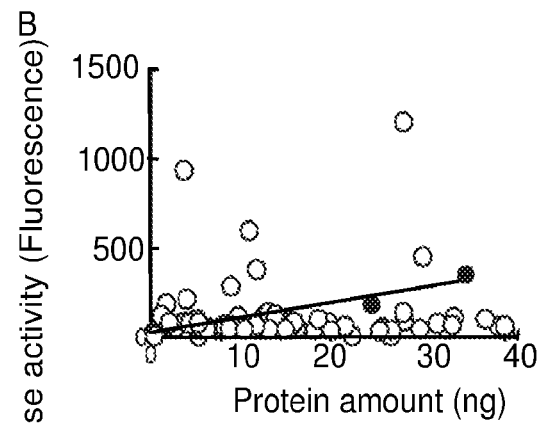
Figure 5:
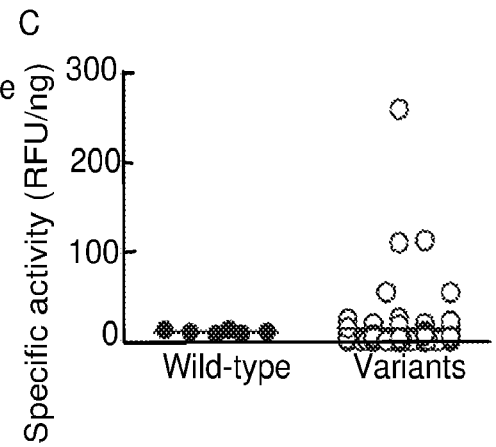

To remove the human beta-glucuronidase variants which cannot properly fold or be expressed on the surface of cells, we first stained live 293/L1 cells with mAb 7G8-FITC which binds to human beta-glucuronidase, and collected the cells which displayed relatively high levels of human beta-glucuronidase protein on their surface. Flow cytometry results indicated that 16% of 293/L1 cells expressed GPI-anchored human beta-glucuronidase on their surface (dashed gate, See FIG. 5, panel A). Cells exhibiting the highest human beta-glucuronidase expression level were sorted as single cells into 96-well microplates (6.8% of the population, solid gate, FIG. 5, panel A) and allowed to expand to near confluence. Each colony was then treated with PI-PLC to cut the GPI anchor and the concentration and activity of each solubilized beta-glucuronidase variant was assayed as described in Materials and Methods. For example, screening of several 96-well microtiter plates revealed three beta-glucuronidase variants that exhibited significantly higher alpha-iduronidase activity than wild-type beta-glucuronidase. See FIG. 5, panels B and C. In total, we screened fifty 96-well plates of sorted 293/L1 library cells and identified 1.3% (73/4800) of beta-glucuronidase variants with elevated alpha-iduronidase activity as compared to wild-type beta-glucuronidase.

Characterization of Human Beta-Glucuronidase Variants Displaying Alpha-Iduronidase Activity Several human beta-glucuronidase variants which exhibited high alpha-iduronidase activity were randomly selected and cloned into a mammalian expression vector to produce greater amounts of recombinant soluble beta-glucuronidase from BALB/3T3 fibroblasts and 34/2000 cells (human alpha-iduronidase deficient fibroblasts derived from a MPS type I patient). All soluble human beta-glucuronidase variants displayed enhanced alpha-iduronidase activity as compared to wild-type beta-glucuronidase and the sequences were analyzed. See Table 1.

Figure 6:
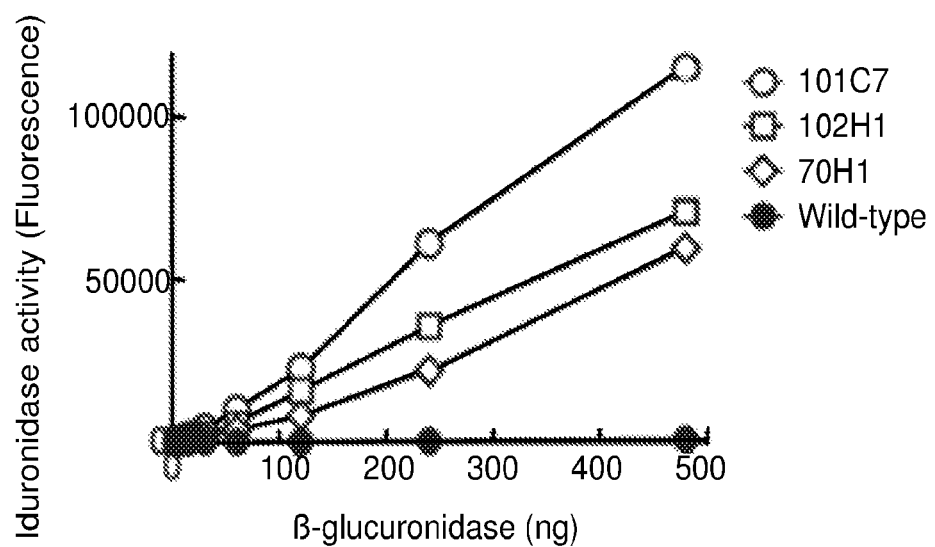
FIG. 6 is a graph showing characterization of beta-glucuronidase variants displaying alpha-iduronidase activity. Recombinant wild-type and beta-glucuronidase variants were incubated with 4-methylumbelliferyl alpha-L-iduronide (MUI) at pH 3.5 and relative fluorescence was detected.

The amino acid sequences of selected clones are shown in Table 2. Three beta-glucuronidase variants, 102H1, 101C7, and 70H1, were further characterized. The recombinant human beta-glucuronidase variants showed similar molecular weights as wild-type human beta-glucuronidase as determined by immunoblotting with anti-6xHis tag antibody. The beta-glucuronidase variants also exhibited increased activity against MUI as compared to wild-type human beta-glucuronidase. See FIG. 6.

iduronidase by a factor ranging from 7900 to 24500-fold. The beta-glucuronidase variants exhibited low but significant alpha-iduronidase activity ranging from 0.3 to 0.9% of wild-type alpha-iduronidase.

TABLE 3

Kinetic parameters of wild-type alpha-iduronidase (IDUA), beta-glucuronidase (βG), and beta-glucuronidase variants for hydrolysis of 4-methylumbelliferyl alpha-L-iduronide (MUI) at pH 3.5

|  | $K_m$ (μM) | $k_{cat}$ ($s^{-1}$) | $k_{cat}/K_M$ ($s^{-1} M^{-1}$) |
|---|---|---|---|
| IDUA | 203 ± 21 | 10.2 ± 0.4 | 50100 ± 3100 |
| Wild-type βG | 705 ± 7.0 | 0.0009 ± 0.0002 | 1.22 ± 0.35 |
| 102H1 | 36.9 ± 3.2 | 0.0099 ± 0.0009 | 270 ± 24 |
| 101C7 | 28.2 ± 2.4 | 0.013 ± 0.0011 | 470 ± 40 |
| 70H1 | 24.5 ± 1.6 | 0.0039 ± 0.0003 | 160 ± 11 |

Results are presented as mean value ± SD of triplicate determinations.

TABLE 2

Amino acid sequences of high alpha-iduronidase activity variants

| Clones | 204 | 279 | 438 | 447 | 484 | 502 | 503 | 504 | 506 | 508 | 509 | 542 |
|---|---|---|---|---|---|---|---|---|---|---|---|---|
| Wild-type | T | Q | K | S | N | N | S | Y | S | Y | H | G |
| 102H1 |  |  |  |  |  | S | D | A |  | G |  | A | D |
| 101C7 |  | H |  |  | C | K | Y | G | G |  | P |  |
| 70H1 |  |  |  |  | D | K | Y |  | G | D | P |  |
| 3D12 |  |  |  |  | R | K | P | G | G | D | A | D |
| 1H9 |  |  |  |  | H |  | P | G |  | D |  |  |
| 4G1 | K |  | M |  | D | K | Y |  | G | D | P |  |
| 5A6 |  |  |  |  | S |  | V | G | G | D |  |  |
| 7H3 |  |  |  |  | R | K | D | C |  |  | P |  |
| 1A8 |  |  | M |  |  | D | K | Y |  | G | D | P |

| Clones | 545 | 565 | 587 | 592 | 594 | 595 | 598 | 600 | 603 | 604 | 606 | 636 |
|---|---|---|---|---|---|---|---|---|---|---|---|---|
| Wild-type | T | L | W | F | T | E | P | R | G | N | K | P |
| 102H1 | A |  |  | Y |  | V |  |  |  | S | F |  |
| 101C7 | A | A |  |  | L | Q |  |  |  | A | F |  |
| 70H1 | A |  |  | Y | L | G | D |  |  | T | F | S |
| 3D12 |  |  | T | Y |  | G |  | A |  | Y | Q |  |
| 1H9 |  |  |  | Y |  | L | D | A | E | S | L |  |
| 4G1 | A |  |  | Y | L | G | D |  |  | T | F |  |
| 5A6 |  |  | T | Y |  | L | D |  |  | S | F |  |
| 7H3 |  | A |  |  |  | L | D |  |  | S | F |  |
| 1A8 | A |  |  | Y | L | G | D |  |  | T | F |  |

The kinetic properties of human beta-glucuronidase variants against MUI were measured and analyzed. See Table 3. The substrate affinity $K_M$ to MUI of the human beta-glucuronidase variants 102H1, 101C7, and 70H1 were 36.9±3.2, 28.2±2.4, and 24.5±1.6 μM, respectively. Compared to wild-type human beta-glucuronidase, these variants showed 19, 25, and 29-fold enhanced affinity to MUI, respectively. The enzyme turnover number $k_{cat}$ of the human beta-glucuronidase variants 102H1, 101C7, and 70H1 were 0.0099±0.0009, 0.013±0.0011, and 0.0039±0.0003, which correspond to 11, 14, and 4-fold improvement as compared to wild-type beta-glucuronidase, respectively. The overall alpha-iduronidase activity of the three beta-glucuronidase variants were increased from 100 to 290-fold as compared to wild-type beta-glucuronidase. See Table 4. The enzyme specificity was shifted from beta-glucuronidase to alpha-

TABLE 4

Relative enzyme activity and specificity change of wild-type and beta-glucuronidase (βG) variants

|  | Relative IDUA activity | Relative βG activity | Specificity shift | Activity relative to wild-type IDUA |
|---|---|---|---|---|
| Wild-type | 1 | 1 | 1 | 0.002% |
| 102H1 | 170 | 0.021 | 7900 | 0.514% |
| 101C7 | 290 | 0.015 | 19200 | 0.895% |
| 70H1 | 100 | 0.004 | 24500 | 0.306% |

The alpha-iduronidase (IDUA) and beta-glucuronidase (βG) activity was assayed with 4-methylumbelliferyl alpha-L-iduronide (MUI) and 4-methylumbelliferyl beta-D-glucuronide (MUG), respectively. The relative enzyme activity was presented in fold increases of $k_{cat}/K_M$ as compared to wild-type alpha-iduronidase and beta-glucuronidase. The specificity shift was presented in fold change of IDUA activity over βG activity compared to wild-type beta-glucuronidase.

Figure 7:
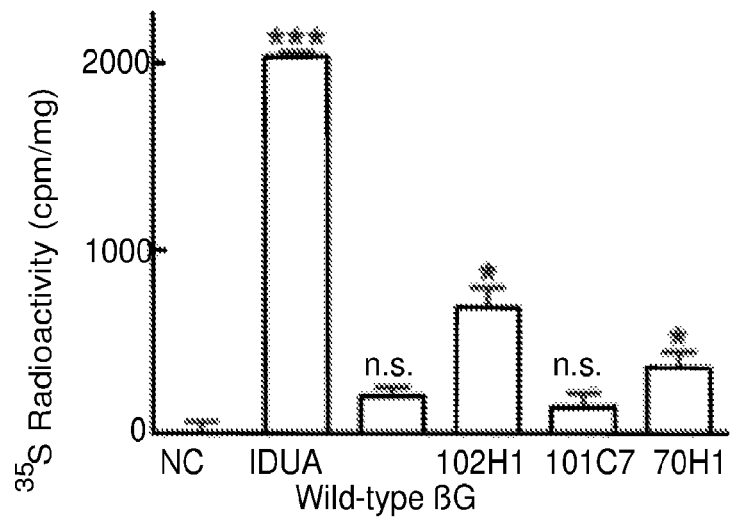
FIG. 7 is a set of graphs showing characterization of beta-glucuronidase variants displaying alpha-iduronidase activity. Human alpha-iduronidase deficient cells (34/2000, derived from a Mucopolysaccharidosis type I patient) were incubated with $Na_2^{35}SO_4$ to radiolabel the glycosaminoglycans. Cells were then treated with 5 μg/ml of recombinant enzymes for 72 h. A. The reduced radioactivity of cell lysates as compared to untreated cells is represented as mean±SD (white bars). B. The increased radioactivity of supernatants as compared to untreated cells is represented as mean±SD (black bars).
Figure 7:
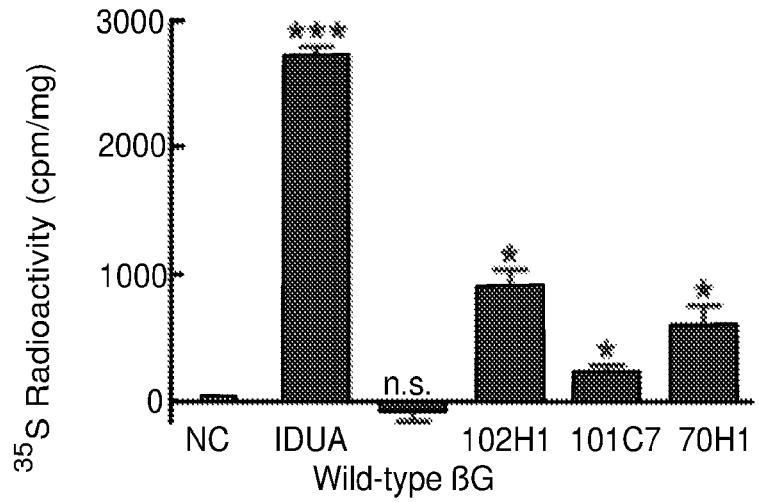

To address whether recombinant human beta-glucuronidase variants could alter the phenotype of MPS I cells, cellular GAG accumulation was measured by a $SO_4^{35}$ incorporation assay. MPS I cells were incubated with $Na_2^{35}SO_4$ to radiolabel GAG before the cells were exposed to 5 µg/ml recombinant enzyme for 72 h. Cell lysates and culture medium were then collected and the $^{35}S$ radioactivity was measured. Cells treated with wild-type alpha-iduronidase or the beta-glucuronidase variants 102H1 and 70H1 exhibited significantly reduced radioactivity in cell lysates as compared to untreated cells. See FIG. 7, panel A. The culture medium of MPS I cells which were treated with wild-type alpha-iduronidase and the three beta-glucuronidase variants exhibited significantly increased radioactivity as compared to cells treated with wild-type beta-glucuronidase (see FIG. 7, panel B), indicative of enhanced digestion and excretion of cellular GAG product. In summary, as compared to untreated cells and cells treated with wild-type beta-glucuronidase, cells treated with beta-glucuronidase variants 102H1 and 70H1 revealed significantly reduced cellular GAG and increased GAG excretion. Cells treated with beta-glucuronidase variant 101C7 displayed a non-statistically significant decrease of cellular GAG but significantly increased GAG excretion. Although the beta-glucuronidase variants were not as effective as wild-type alpha-iduronidase, these results indicate partial correction of GAG storage in MPS I cells.

Figure 8:
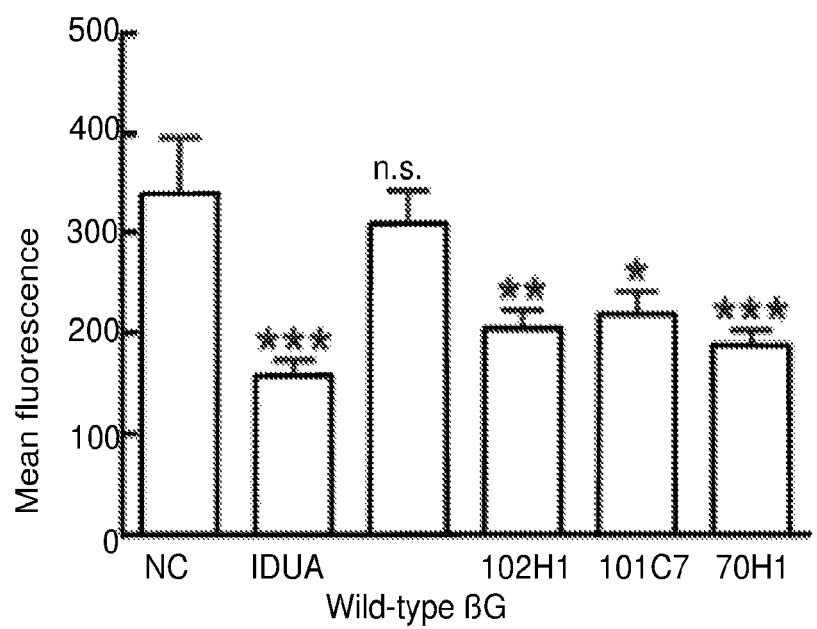
FIG. 8 is a graph showing characterization of beta-glucuronidase variants displaying alpha-iduronidase activity. Human alpha-iduronidase deficient cells were treated with 5 μg/ml of recombinant enzymes for 72 h and stained with Lysotracker-Red DND-99 dye for lysosomes. Lysosomal fluorescence per cell is presented as mean±SEM. Statistically significant differences to untreated cells in two-tailed t-test are indicated. *: $p<0.05$; : $p<0.01$; *: $p<0.001$; n.s.: non-significant (n=3).

We also employed a qualitative lysosomal staining method to visualize the phenotypic change in MPS I cells. MPS I cells were incubated with 5 µg/ml of recombinant enzymes for 72 h and then stained with Lysotracker-red DND-99 dye (Invitrogen, Carlsbad, Calif., USA) to visualize the lysosomes (data not shown). The lysosome fluorescence was quantitated as mean fluorescence intensity per cell. High lysosomal staining was observed in non-treated MPS I cells. As expected, treatment of the cells with wild-type beta-glucuronidase did not affect lysosome fluorescence. By contrast, the cells treated with alpha-iduronidase or beta-glucuronidase variants (102H1, 101C7, and 70H1) displayed significantly reduced lysosomal staining as compared to non-treated MPS I cells (see FIG. 8), indicating at least partial normalization of lysosomes in the deficient cells. In summary, these results revealed that beta-glucuronidase variants displayed beneficial effects toward correction of the phenotype of MPS I cells.

The beta-glucuronidase variants are expected to display reduced immunogenicity as compared to alpha-iduronidase in MPS I patients because only several amino acids are changed from the wild-type beta-glucuronidase sequence. For example, the selected beta-glucuronidase variants 102H1, 101C7, and 70H1 possess 11, 13, and 13 amino acid changes, which corresponds to 1.7, 2, and 2% of the total amino acids. Besides, these mutations are mostly buried in the interior active pocket and may be inaccessible to antibodies.

Figure 9:
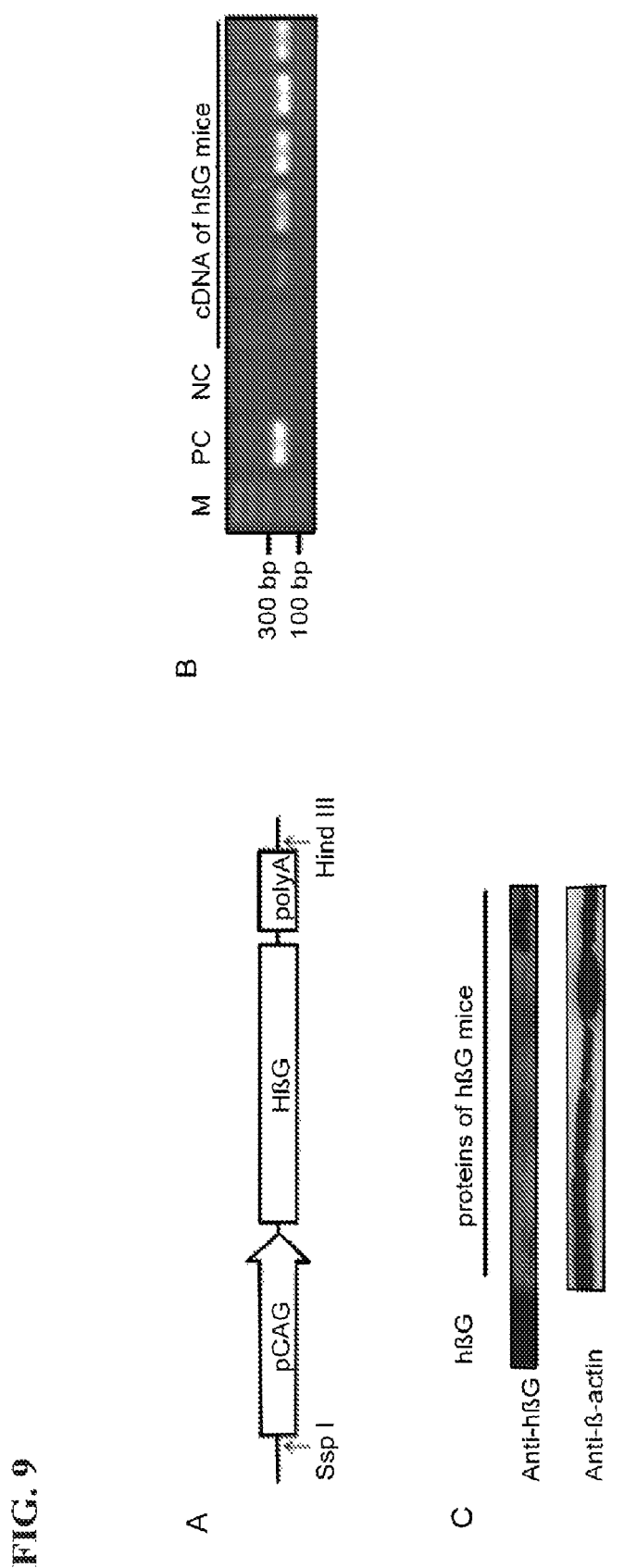
FIG. 9 is a set of data showing establishment of human beta-glucuronidase transgenic mice. A. An illustration showing pCAG-hβG for generation of transgenic mice expressing human beta-glucuronidase. B. Genotyping of newborn mice was performed by genomic PCR (230 bp). PC: positive control. NC: negative control. C. Total proteins were extracted from mouse tails, electrophoresed on a 10% SDS-PAGE, and immunoblotted with anti-human beta-glucuronidase (anti-hβG) and anti-β-actin antibodies.

Immunogenicity of Human Beta-Glucuronidase Variants in Human Beta-Glucuronidase Transgenic Mice To investigate the immunogenicity of the beta-glucuronidase variants, an appropriate animal model such as a human beta-glucuronidase transgenic mouse is very useful. Human beta-glucuronidase transgenic mice can mimic MPS I patients, who express normal human beta-glucuronidase but not human alpha-iduronidase. These mice can be used to investigate the immunogenicity of human beta-glucuronidase variants as well as to test if host autoimmune responses to endogenous human beta-glucuronidase is induced. We thus generated transgenic mice that express human beta-glucuronidase. See FIG. 9.

To determine whether human beta-glucuronidase is tolerant in the transgenic mice, 50 µg of recombinant proteins (i.e., human beta-glucuronidase, mouse beta-glucuronidase, human alpha-iduronidase, human beta-glucuronidase variant 101C7, and human beta-glucuronidase variant 70H1) were intravenously injected into transgenic mice every three weeks for a total of 4 injections. Serum antibodies against the administered proteins were determined by ELISA.

Figure 10:
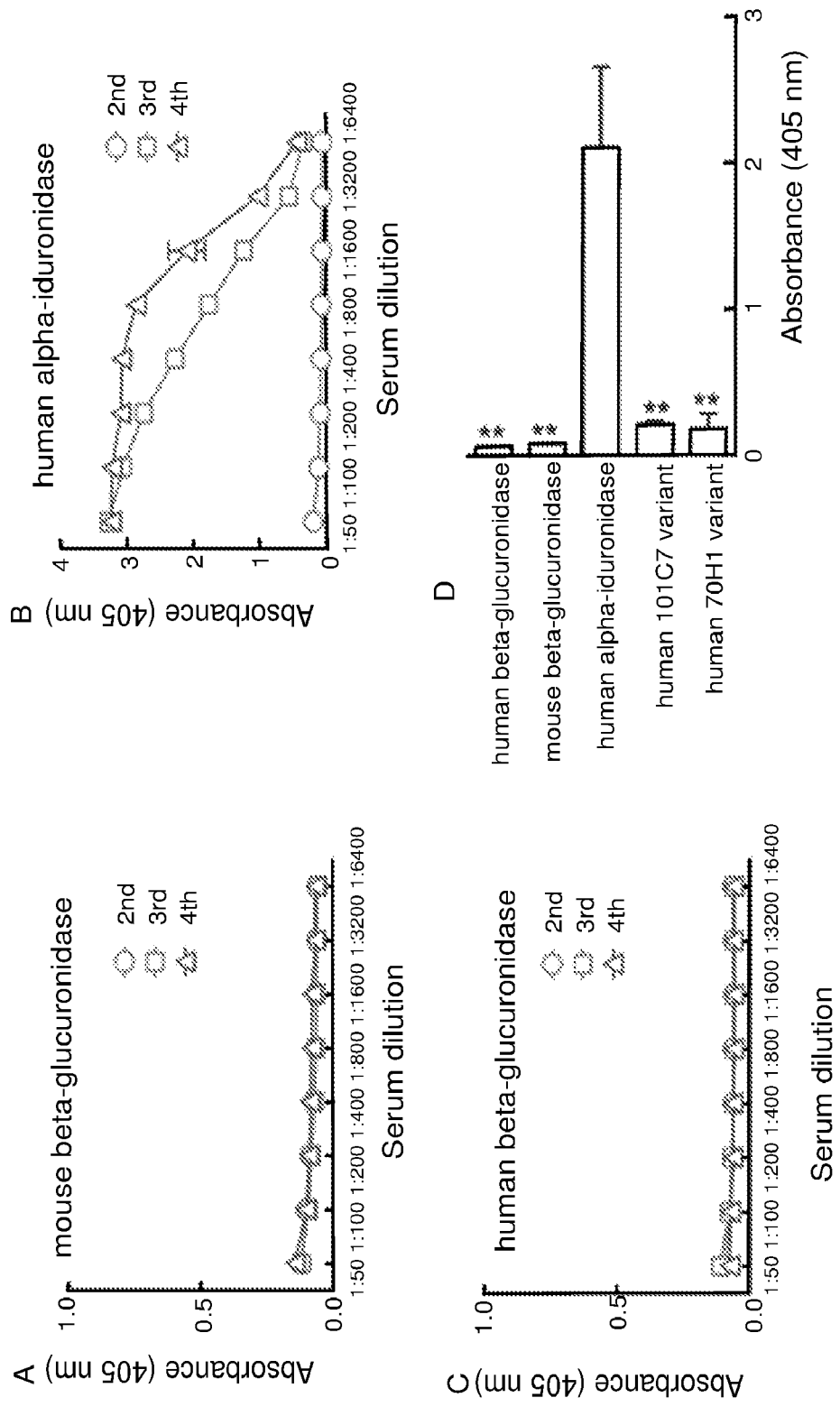
FIG. 10 is a set of graphs showing evaluation of engineered beta-glucuronidase immunogenicity in transgenic human beta-glucuronidase mice. A, B, and C. Groups of three human beta-glucuronidase transgenic mice were i.v. injected with 50 μg mouse beta-glucuronidase, 50 μg of human alpha-iduronidase or 50 μg human beta-glucuronidase every three weeks. Weekly serum samples were assayed for antibodies against the respective protein by ELISA. D. Groups of three human beta-glucuronidase transgenic mice were i.v. injected with 50 μg of the indicated recombinant protein every three weeks for a total of four injections. Serum samples were diluted 1000 fold and antibody responses were measured by ELISA. Significant differences between the antibody response in mice injected with human alpha-iduronidase and other proteins are shown. **, $p<0.001$.

As expected, the mice tolerated repeated injections of mouse beta-glucuronidase (see FIG. 10, panel A), but developed antibodies against human alpha-iduronidase (see FIG. 10, panel B). By contrast, the mice did not generate antibodies against human beta-glucuronidase (see FIG. 10, panel C), indicating that human beta-glucuronidase appeared as a self-antigen. Two human beta-glucuronidase variants that display alpha-iduronidase activity (101C7 and 70H1) displayed significantly less immunogenicity in the transgenic mice than wild-type alpha-iduronidase (see FIG. 10, panel D), suggesting that the "cloaked stealth" approach may help reduce the immunogenicity of enzyme replacement therapy.

In summary, the transgenic mice express human beta-glucuronidase and were well tolerant to administration of wild-type human beta-glucuronidase. This animal model readily mimicked MPS I patients who express normal beta-glucuronidase but not alpha-iduronidase.

Materials and Methods

Reagents and Antibodies

Phosphatidylinositol-specific phospholipase C (PI-PLC), Lysotracker-Red DND-99 dye and Hoechst 33342 nuclear dye were from Invitrogen (Carlsbad, Calif., USA). 4-methylumbelliferyl beta-D-glucuronide (MUG) was from Sigma-Aldrich (St. Louis, Mo., USA). 4-methylumbelliferyl alpha-L-iduronide (MUI) was from USB Corporation (Cleveland, Ohio, USA). Trace MUG contamination (~2%) in commercial MUI was removed by solid-phase extraction/high-performance liquid chromatography on a LiChroprep RP18 (40-63 µm) column equilibrated with 20% methanol (pH 4). MUI was eluted with 25% methanol in double-distilled water (pH 4) and condensed in a rotavapor. Mouse anti-human beta-glucuronidase monoclonal antibody (mAb) 7G8 was directly labelled with FITC or biotin as described [34, 35]. Streptavidin-horse radish peroxidase (HRP) was from Jackson ImmunoResearch (West Grove, Pa., USA).

Cell Culture

GP293V cells (derived from human embryonic kidney 293 cells) were kindly provided by Dr. Andre Lieber, University of Washington, Seattle, Wash. 34/2000 cells (human alpha-iduronidase deficient fibroblasts derived from a MPS type I patient) were a kind gift from Dr. Mirella Filocamo, Istituto G Gaslini, Genova, Italy. BALB/3T3 fibroblasts and HEK293 cells were obtained from ATCC (Manassas, Va., USA). Cells were cultured in Dulbecco's minimal essential medium (DMEM) supplemented with 10% fetal bovine serum, 2.98 g/L HEPES, 2 g/L $NaHCO_3$, 100 U/ml penicillin, and 100 µg/ml streptomycin.

Structure Analysis of Human Beta-Glucuronidase and Alpha-Iduronidase

The protein structural alignment of human beta-glucuronidase, human alpha-iduronidase and *Thermoanaerobacterium saccharolyticum* beta-xylosidase indicated that they have conserved catalytic glutamic acid residues. 3D structures of human beta-glucuronidase (PDB ID: 1BHG), a human alpha-iduronidase homology model deduced from

*Thermoanaerobacterium saccharolyticum* beta-xylosidase (PDB ID: 1Y24), and *Thermoanaerobacterium saccharolyticum* beta-xylosidase (PDB ID: 1PX8) were also used in the analysis. The catalytic TIM $(\beta/\alpha)_8$-barrel domains were superimposed and analyzed by PyMOL and OPAAS, respectively. Although the whole protein structures of human beta-glucuronidase and alpha-iduronidase do not closely resemble each other, these proteins share a common TIM $(\beta/\alpha)_8$-barrel structure and conserved glutamic acid residues in their catalytic pockets. Residues predicted to contact substrates were selected for mutation.

Synthetic Library Construction

A human beta-glucuronidase library with mutations at nineteen residues for a total diversity of $3\times10^9$ was designed. Fifteen residues (S447, N484, N502, S503, Y504, Y508, H509, G542, W587, F592, T594, E595, R600, N604, and K606) in the beta-glucuronidase catalytic domain were identified as surrounding the active pocket in which substrates were accommodated. Previous research also reported several beta-glucuronidase residues associated with enzyme activity and specificity (N484, S503, S506, H509, T545, L565, E595, P598, N604, and K606). A total of nineteen amino acid residues were mutated. See Table 1. The six underlined residues (N484, S503, H509, E595, N604, and K606) were considered as hot spots because they were identified by both structure analysis and a review of the literature. The six hot spots were mutated to variable amino acids to enrich the library diversity. For example, we employed degenerate primers at S503 to mutate serine into amino acids with side chains which are positively charged (histidine), negatively charged (aspartic acid), aromatic (tyrosine and phenylalanine), hydrophobic (alanine, leucine and valine), and special in conformation (proline). The other residues were mutated to the corresponding amino acids which were identified from the structural comparison or in previous studies (Table 1). Primer assembly was used to generate the human beta-glucuronidase library (see FIG. 4). Briefly, the full-length beta-glucuronidase sequence was divided into five fragments with 18 overlapping nucleotides between each other (F0-4). The F0 fragment contained an Apa I cloning site as well as a silent mutation (nucleotide G741A) to remove a unique Bgl II cutting site in the human beta-glucuronidase gene to remove wild-type DNA contamination after library construction. The wild-type fragment F1 simply served as a bridge between the F0 and F2 fragments. The F2 and F3 fragments, which contained variable amino acids at nineteen positions, were constructed by primer assembly followed by PCR amplification. The wild-type F4 fragment contained a Sal I cloning site. All fragments were mixed in the same molar ratio and amplified by PCR to obtain a full-length beta-glucuronidase library which was digested with Apa I and Sal I and ligated into the same sites in pLNCX-hβG-DAF to append a sequence coding for a GPI anchor to the C-terminus of the enzyme variants. The DNA library was digested by Bgl II to remove any wild-type DNA contamination and then transformed into DH5α competent cells by electroporation. Transformed bacteria were selected on 15-cm carbenicillin-containing LB agar plates for 16 h at 37° C. Plasmid DNA was purified from single colonies and sequenced to determine the mutation rates at selected residues. All expected mutations were present in the synthetic library. Colonies from multiple plates were collected and expanded in carbenicillin-containing LB medium. The plasmid was amplified by addition of chloramphenicol to a final concentration 170 μg/ml when $OD_{600}$ was 0.5. After overnight culture, plasmid DNA was purified by centrifugation in a CsCl-ethidium bromide density gradient at 60,000 rpm in a Ti 70.1 rotor for 24 h at 4° C. using a Beckman Optima L-90K ultracentrifuge (Beckman Coulter, Fullerton, Calif., USA).

Generation of Stable Library Cells

To generate stable cell libraries, library plasmid DNA was cotransfected with pVSV-G (Clontech, Mountain View, Calif., USA) into GP293V cells to produce recombinant retroviral particles. Two days after transfection, the culture medium was filtered, mixed with 8 μg/ml polybrene, and incubated with 293 cells at a multiplicity of infection of 0.1. Stable cell lines were selected in medium containing 0.5 mg/ml G418 (Calbiochem, San Diego, Calif., USA). The resulting synthetic library cells were denoted as 293/L1 cells.

Flow Cytometer Analysis and Library Cell Selection

Human beta-glucuronidase surface expression was determined by staining 293/L1 cells with 7G8-FITC, which binds to human beta-glucuronidase, and measuring immunofluorescence of viable cells with a FACScaliber flow cytometer (BD Biosciences, Franklin Lakes, N.J., USA). Generally, $2\times10^7$ cells were washed and suspended in 1 ml HBSS (5.4 mM KCl, 0.3 mM $Na_2HPO_4$, 0.4 mM $KH_2PO_4$, 4.2 mM $NaHCO_3$, 1.3 mM $CaCl_2$, 0.5 mM $MgCl_2$, 0.6 mM $MgSO_4$, 137 mM NaCl, 5.6 mM D-glucose, pH 7.4) containing 0.5% BSA and 20 μg/ml 7G8-FITC for 30 min at 4° C. The cells were washed with ice-cold HBSS containing 0.5% BSA and suspended in 0.5% BSA/HBSS containing 5 μg/ml propidium iodide. Cells were sorted on a FACSAria cell sorter (BD Biosciences, Franklin Lakes, N.J., USA). Dead cells (propidium iodide positive, high FL3 fluorescence) were gated out before 7G8-FITC immunofluorescence was detected at excitation/emission wavelengths of 488/515 nm (FL1). Single cells expressing surface human beta-glucuronidase were sorted into 96-well microplates in Dulbecco's minimal essential medium supplemented with 10% bovine serum.

Surface Enzyme Release and Enzyme Activity Screening

293/L1 cells in 96-well microplates were washed once with PBS and incubated with 100 μl PBS containing 50 mU/mL phosphatidylinositol phospholipase C (PI-PLC) at 37° C. for 1 h to cleave GPI-anchored beta-glucuronidase variants from surface of the cells. Alpha-iduronidase activity of the released beta-glucuronidase was assayed by mixing 20 μl samples of cleaved enzyme with 80 μl of 50 μM 4-methylumbelliferyl alpha-L-iduronide (MUI) in 0.2 M formate buffer, pH 3.5 for 17 h at 37° C. The reaction was stopped by adding 100 μl stop buffer (1 M glycine, 0.5 M sodium bicarbonate, pH 10.7) and the 4-methylumbelliferone (4-MU) fluorescence in the wells was measured at an excitation wavelength of 355 nm and an emission wavelength of 460 nm. To reduce the systematic error of manual volumetric transfers during large scale MUI assay and sandwich ELISA, an automated liquid handling system, MicroLab MPH-96 (Hamilton Robotics, Reno, Nev., USA), was employed. Kinetic parameters against MUI were determined by hydrolysis of serial diluted substrate (400 μM) with defined concentrations of enzymes. The reaction was terminated at various time points and the fluorescence was measured. The acquired fluorescence was converted to product concentration by comparison with a 4-MU standard curve. Lineweaver-Burk plots were used to determine $K_M$ and $k_{cat}$.

Sandwich Enzyme-Linked Immunosorbent Assay (ELISA)

The concentration of soluble beta-glucuronidase generated by PI-PLC cleavage of surface enzyme from individual colonies of the sorted 293-L1 cells was measured by sandwich ELISA. 0.1 μg mAb 7G8 in 50 μl coating buffer (50 mM $Na_2CO_3$, 50 mM $NaHCO_3$, pH 8) was incubated in each well of 96-well ELISA plates at room temperature for 1 h. The plates were washed 3 times with PBS and then blocked with 2.5% skim milk in PBS at room temperature for 1 h. The plates were washed 3 times with PBS and a 20 µl human beta-glucuronidase variant sample diluted to 50 µl with PBS was transferred to each well for 1 h at room temperature. The plates were washed 3 times with PBS containing 0.05% Tween 20 before 20 ng 7G8-biotin and 50 ng streptavidin-HRP in 50 µl PBS containing 2.5% skim milk were each subsequently added at room temperature for 1 h. After each step, the plates were washed 3 times with PBS containing 0.05% Tween 20. 150 µl freshly prepared 2, 2'-azino-bis (3-ethylbenzthiazoline-6-sulphonic acid) ABTS substrate was added at room temperature for 30 mM and the absorbance of each well was measured at 405 nm.

Lysosome Staining and Image Acquisition

A lysosomal staining method was employed to visualize the enzyme effect in MPS I cells. Briefly, MPS I cells were plated in 96-well microplates and incubated with 5.0 µg/ml of recombinant enzymes for 72 h. Cells were washed with PBS and live stained with 100 µl medium containing 100 nM Lysotracker-red DND-99 dye and 1 µg/mL Hoechst 33342 for 30 min at 37° C. The cells were washed twice with PBS, replenished with 200 µl DMEM without phenol red and live imaged on an ImageXpress Micro XL High-Content Screening System (Molecular Devices, Calif., USA). The Lysotracker and Hoechst staining were visualized using TRITC (Em=545±20, Ex=593±20 nm) and DAPI (Ex=350±50, Em=455±50 nm) filters, respectively. Nine sites of images per well were recorded and analyzed by MetaXpress High Content Image Acquisition & Analysis Software (Molecular Devices, Calif., USA).

Statistical Analysis

The two-tailed student t-test was used to calculate the significant differences between wild-type and beta-glucuronidase variants by Graphpad Prism 5.0 (GraphPad Software Inc., San Diego, Calif., USA). Data were considered significant at P values less than 0.05.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. An engineered enzyme, comprising an amino acid sequence that is at least 80% identical to the amino acid sequence of a human beta-glucuronidase having SEQ ID NO:2 and an amino acid substitution, in which residue 204 is T or K; residue 279 is Q or H; residue 438 is K or M; residue 484 is S, D, H, R, S, or C; residue 502 is N, D, or K; residue 503 is A, D, Y, P, H, or V; residue 504 is Y, G, or C; residue 506 is S or G; residue 508 is Y or D; residue 509 is H, A, or P; residue 542 is G or D; residue 545 is T or A; residue 565 is L or A; residue 587 is W or T; residue 592 is F or Y; residue 594 is T or L; residue 595 is L, V, Q, or G; residue 598 is P or D; residue 600 is R or A; residue 603 is G or E; residue 604 is Y, S, A, or T; residue 606 is Q, F, or L; and residue 636 is P or S, wherein the engineered enzyme exhibits a higher level of alpha-iduronidase enzymatic activity as compared to the human beta-glucuronidase.

2. The engineered enzyme of claim 1, wherein the engineered enzyme comprises a substitution at N484, N502, S503, S506, H509, F592, E595, N604, and/or K606.

3. The engineered enzyme of claim 1, wherein the engineered enzyme does not have a substitution at a residue that corresponds to residue S447, G542, L565, W587, R600, G603, and/or P636 of the sequence of SEQ ID NO:2.

4. The engineered enzyme of claim 1, wherein the engineered enzyme comprises residues S484, D502, A503, G506, A509, D542, A545, Y592, V595, S604, and/or F606.

5. The engineered enzyme of claim 1, wherein the engineered enzyme comprises residues H279, C484, K502, Y503, G504, G506, P509, A545, A565, L594, Q595, A604, and/or F606.

6. The engineered enzyme of claim 1, wherein the engineered enzyme comprises residues D484, K502, Y503, G506, D508, P509, A545, Y592, L594, G595, D598, T604, F606, and/or S636.

7. A pharmaceutical composition comprising the engineered enzyme of claim 1 and a pharmaceutically acceptable carrier.

8. A method of treating mucopolysaccharidosis in a subject, comprising administering to a subject in need thereof the engineered enzyme of claim 1.

* * * * *